US008735630B2

(12) United States Patent
Buchwald et al.

(10) Patent No.: US 8,735,630 B2
(45) Date of Patent: May 27, 2014

(54) TRANSITION-METAL-CATALYZED CARBON-NITROGEN AND CARBON-CARBON BOND-FORMING REACTIONS

(71) Applicant: Massachusetts Institute of Technology, Cambridge, MA (US)

(72) Inventors: Stephen L. Buchwald, Newton, MA (US); Kevin W. Anderson, Hackettstown, NJ (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 13/768,124

(22) Filed: Feb. 15, 2013

(65) Prior Publication Data

US 2013/0178632 A1    Jul. 11, 2013

Related U.S. Application Data

(62) Division of application No. 12/502,749, filed on Jul. 14, 2009, now Pat. No. 8,378,145, which is a division of application No. 11/328,426, filed on Jan. 9, 2006, now Pat. No. 7,560,596.

(60) Provisional application No. 60/642,774, filed on Jan. 10, 2005.

(51) Int. Cl.
*C07F 9/50* (2006.01)

(52) U.S. Cl.
USPC .......................................................... 568/17

(58) Field of Classification Search
None
See application file for complete search history.

(56) References Cited

U.S. PATENT DOCUMENTS

| 6,307,087 B1 | 10/2001 | Buchwald et al. |
| 6,946,560 B2 | 9/2005 | Buchwald et al. |
| 7,026,498 B2 | 4/2006 | Buchwald et al. |
| 7,247,731 B2 | 7/2007 | Buchwald et al. |

FOREIGN PATENT DOCUMENTS

| WO | WO-03/006420 A1 | 1/2003 |
| WO | WO-2004/052939 A2 | 6/2004 |

OTHER PUBLICATIONS

Gelman et al. Angewandte Chemie, 2003, 42, 5993-5996.*
Erdelyi et al J. Org. Chem., 2001, 66, 4165-4169.*
Dubbaka et al. Adv. Synth. Catal, 2004, 346, 1793-1797.*
Anderson, K. W. et al., "General Catalysts for the Suzuki-Miyaura and Songashira Coupling Reactions of Aryl Chlorides and for the Coupling of Challenging Substrate Combinations in Water", *Angew. Chem. Int. Ed.*, 44:6173-6177 (2005).
Barder, T. E. et al., "Efficient Catalyst for the Suzuki-Miyaura Coupling of Potassium Aryl Trifluoroborates with Aryl Chlorides", *Organic Letters*, 6(16):2649-2652 (2004).
Devasher, R. B. et al., "Aqueous-Phase, Palladium-Catalyzed Cross-Coupling of Aryl Bromides under Mild Conditions, Using Water-Soluble, Sterically Demanding Alkylphosphines", *J. Org. Chem.*, 69:7919-7927 (2004).
Fox J. M. et al., "Highly Active and Selective Catalysts for the Formation of α-Aryl Ketones," *J. Am. Chem. Soc.* 122: 1360-1370 (2000).
Gelman, D. et al., "Efficient Palladium-Catalyzed Coupling of Aryl Chlorides and Tosylates with Terminal Alkynes: Use of a Copper Cocatalyst Inhibits the Reaction", *Angew. Chem. Int. Ed.*, 42:5993-5996 (2003).
Lee, S. et al., "Palladium-Catalyzed Synthesis of Arylamines from Aryl Halides and Lithium Bis(trimethylsilyl)amide as an Ammonia Equivalent", *Org. Lett.*, 3(17):2729-2732 (2001).
Stambuli, J.P. et al., "Screening of Homogeneous Catalysts by Fluorescence Resonance Energy Transfer. Identification of Catalysts for Room-Temperature Heck Reactions", *J. Am. Chem. Soc.*, 123:2677-2678 (2001).
Stauffer, S.R. et al., "Palladium-Catalyzed Arylation of Ethyl Cyanoacetate. Fluorescence Resonance Energy Transfer as a Tool for Reaction Discovery", *J. Am. Chem. Soc.*, 123:2677-2678 (2001).
Strieter, E.R. et al., "Insights into the Origin of High Activity and Stability of Catalysts Derived from Bulky, Electron-Rich Monophosphinobiaryl Ligands in the Pd-Catalyzed C-N Bond Formation", *J. Am. Chem. Soc.*, 125:13978-13980 (2003).
Tomori, H. et al., "An Improved Synthesis of Functionalized Biphenyl-Based Phosphine Ligands.", *J. Org. Chem.*, 65:5334-5341 (2000).
Walker, S. D. et al., "A Rationally Designed Universal Catalyst for Suzuki-Miyaura Coupling Processes", *Angew. Chem. Int. Ed.*, 43:1871-1876 (2004).
Supplementary European Search Report dated Jul. 15, 2008 for EP 03 812 849.
International Search Report dated Jul. 12, 2006 for PCT/US2006/000365.

* cited by examiner

*Primary Examiner* — Yevegeny Valenrod
(74) *Attorney, Agent, or Firm* — Alan W. Steele; Foley Hoag LLP

(57) ABSTRACT

One aspect of the present invention relates to ligands for transition metals. A second aspect of the present invention relates to the use of catalysts comprising these ligands in various transition-metal-catalyzed carbon-heteroatom and carbon-carbon bond-forming reactions. The subject methods provide improvements in many features of the transition-metal-catalyzed reactions, including the range of suitable substrates, number of catalyst turnovers, reaction conditions, and efficiency. For example, improvements have been realized in transition metal-catalyzed: aryl amination reactions; aryl amidation reactions; Suzuki couplings; and Sonogashira couplings. In certain embodiments, the invention relates to catalysts and methods of using them that operate in aqueous solvent systems.

7 Claims, 8 Drawing Sheets

Figure 2

| Entry | Halide | Boronic Acid | Product | Pd (mol %) | Conditions | Yield (%)[b] |
|---|---|---|---|---|---|---|
| 1 | 4-chloro-o-xylene | PhB(OH)₂ | 3,4-dimethylbiphenyl | 2 | r.t., 10 h | 99 |
| 2 | 3-chlorobenzamide | 2,6-dimethylphenylB(OH)₂ | 2',6'-dimethyl-3-biphenylcarboxamide | 1 | 100 °C, 8 h | 99 |
|   |   |   |   | 1 | 150 °C (μW), 10 min. | 94[c] |
| 3 | 3-chlorobenzoic acid | PhB(OH)₂ | 3-biphenylcarboxylic acid | 2 | r.t., 2 h | 96 |
|   |   |   |   | 0.5 | r.t., 8 h | 97 |
|   |   |   |   | 0.1 | 100 °C, 5 h | 97 |
|   |   |   |   | 0.1 | 150 °C (μW), 10 min. | 98[c] |
| 4 | 3-chlorobenzoic acid | 2-methylphenylB(OH)₂ | 2'-methyl-3-biphenylcarboxylic acid | 0.5 | r.t., 8 h | 95 |
|   |   |   |   | 0.1 | 100 °C, 6 h | 96 |
| 5 | 5-chloro-2-hydroxybenzoic acid | 2-methylphenylB(OH)₂ | 4-hydroxy-2'-methyl-3-biphenylcarboxylic acid | 2 | r.t, 12 h | 99[d] |
|   |   |   |   | 0.1 | 100, 12 h | 96[d] |
| 6 | 2-bromo-1,3,5-trimethylbenzene | 2-methylphenylB(OH)₂ | 2,2',4,6-tetramethylbiphenyl | 2 | r.t., 22 h | 94 |
| 7 | 2-bromotoluene | 2,6-dimethylphenylB(OH)₂ | 2,2',6'-trimethylbiphenyl | 2 | r.t, 22 h | 97 |

Figure 3

| Entry | Halide | Boronic Acid | Product | Yield (%)[b] |
|---|---|---|---|---|
| 1 | HO₂C–⟨⟩–Cl | (HO)₂B–⟨⟩–CO₂H | HO₂C–⟨⟩–⟨⟩–CO₂H | 99[c] 95[d] |
| 2 | HO₂C–⟨⟩–Cl | (HO)₂B–⟨⟩–OH | HO₂C–⟨⟩–⟨⟩–OH | 99 |
| 3 | HO₂C–⟨⟩–Cl | (HO)₂B–⟨⟩–R | HO₂C–⟨⟩–⟨⟩–R | R = NH₂  94<br>C(O)Me  97<br>CHO  87[e] |
| 4 | HO₂C,HO–⟨⟩–Cl | (HO)₂B–⟨⟩–CN | HO₂C,HO–⟨⟩–⟨⟩–CN | 92[f] |
| 5 | HO₂C–⟨⟩(NH₂)–Cl | (HO)₂B–⟨⟩–NH₂ | HO₂C–⟨⟩(NH₂)–⟨⟩–NH₂ | 93 |
| 6 | HO₃S–⟨⟩–Cl | (HO)₂B–Me | HO₃S–⟨⟩–Me | 97 |
| 7 | H₂NO₂S–⟨⟩–Cl | (HO)₂B–⟨⟩(F,F) | H₂NO₂S–⟨⟩–⟨⟩(F,F) | 96 |

Figure 4

| Entry | Halide | Boronic Acid | Product | Yield (%)[b] |
|---|---|---|---|---|
| 1 | 4-chloro-3,5-dimethylphenol | dibenzo[b,d]thiophene/dioxin-boronic acid | biaryl product | 93 |
| 2 | 5-chloro-1H-indole-2-carboxylic acid | (4-methoxyphenyl)boronic acid | 5-(4-methoxyphenyl)-1H-indole-2-carboxylic acid | 93[c] |
| 3 | 2-(4-chlorophenoxy)nicotinic acid | (3-acetylphenyl)boronic acid | biaryl product | 92[c] |
| 4 | 2-amino-5-chloropyridine | pyridin-3-ylboronic acid | 2-amino-5-(pyridin-3-yl)pyridine | 93 |
| 5 | 5-bromothiophene-2-carboxylic acid | furan-3-ylboronic acid | 5-(furan-3-yl)thiophene-2-carboxylic acid | 97<br>95[d] |

| Entry | Ligand | Solvent | T (°C) | Conv. (%) | Yield (%)[b] |
|-------|--------|---------|--------|-----------|--------------|
| 1 | 1 | n-BuOH | 100 | 77 | 75 |
| 2 | 1 | n-BuOH/H$_2$O (5:1) | 100 | 27 | 26 |
| 3 | 1 | propionitrile/H$_2$O (1:1) | 100 | >99 | 96 |
| 4 | 1 | N,N-DMF/H$_2$O (1:1) | 100 | >99 | 94 |
| 5 | 1 | CH$_3$CN/H$_2$O (1:1) | r.t. | 17 | 12 |
| 6 | 1 | H$_2$O | 100 | 22 | 20 |
| 7 | 2 | H$_2$O | r.t. | >99 | 97[c] |

| Entry | Halide | Alkyne | Product | Yield (%)[b] |
|---|---|---|---|---|
| 1 | 3-MeO-C₆H₄-Br | ≡—CO₂H | 3-MeO-C₆H₄-≡—CO₂H | 70[c,d] |
| 2 | 3-HO₂C-C₆H₄-Br | ≡—CO₂H | 3-HO₂C-C₆H₄-≡—CO₂H | 69[c,d] |
| 3 | 4-HO₂C-C₆H₄-Cl | ≡—C₈H₁₇ | 4-HO₂C-C₆H₄-≡—C₈H₁₇ | 86 |
| 4 | 3-MeO-C₆H₄-Cl | ≡—(CH₂)₃CO₂H | 3-MeO-C₆H₄-≡—(CH₂)₃CO₂H | 85[d] |
| 5 | 3,5-F₂-4-HO₂C-C₆H₂-Cl | ≡—C₈H₁₇ | 3,5-F₂-4-HO₂C-C₆H₂-≡—C₈H₁₇ | 71 |
| 6 | 3-MeO-C₆H₄-Cl | ≡—Ph | 3-MeO-C₆H₄-≡—Ph | 88 |
| 7 | 3-Cl-pyridine | ≡—(3-thienyl) | 3-pyridyl-≡—(3-thienyl) | 93 |
| 8 | 4-HO₂C-C₆H₄-Cl | ≡—Ph | 4-HO₂C-C₆H₄-≡—Ph | 96[d] |

TRANSITION-METAL-CATALYZED CARBON-NITROGEN AND CARBON-CARBON BOND-FORMING REACTIONS

This application is a divisional of U.S. patent application Ser. No. 12/502,749, filed Jul. 14, 2009; which is a divisional of U.S. patent application Ser. No. 11/328,426, filed Jan. 9, 2006, now U.S. Pat. No. 7,560,596; which claims the benefit of priority to U.S. Provisional Patent Application Ser. No. 60/642,774, filed Jan. 10, 2005; all hereby incorporated by reference in their entireties.

STATEMENT REGARDING FEDERALLY SPONSORED RESEARCH OR DEVELOPMENT

This invention was made with government support under Grant No. RO1 GM058160 awarded by the National Institutes of Health. The government has certain rights in the invention.

BACKGROUND OF THE INVENTION

Transition metal catalyst complexes play important roles in many areas of chemistry, including the preparation of polymers and pharmaceuticals. The properties of these catalyst complexes are recognized to be influenced by both the characteristics of the metal and those of the ligands associated with the metal atom. For example, structural features of the ligands can influence reaction rate, regioselectivity, and stereoselectivity. Bulky ligands can be expected to slow reaction rate; electron-withdrawing ligands, in coupling reactions, can be expected to slow oxidative addition to, and speed reductive elimination from, the metal center; and electron-rich ligands, in coupling reactions, conversely, can be expected to speed oxidative addition to, and slow reductive elimination from, the metal center.

In many cases, the oxidative addition step in the accepted mechanism of a coupling reaction is deemed to be rate limiting. Therefore, adjustments to the catalytic system as a whole that increase the rate of the oxidative addition step should increase overall reaction rate. Additionally, the rate of oxidative addition of a transition metal catalyst to the carbon-halogen bond of an aryl halide is known to decrease as the halide is varied from iodide to bromide to chloride, all other factors being equal. Because of this fact, the more stable, lower molecular weight, and arguably more easy to obtain, members of the set of reactive organic halides—the chlorides—are typically the poorest substrates for traditional transition metal catalyzed coupling reactions and the like. In many cases, the best halogen-containing substrates for transition metal catalyzed carbon-heteroatom and carbon-carbon bond forming reactions have been the iodides. Bromides have often been acceptable substrates, but have often required higher temperatures, longer reaction times, and have given lower yields of products.

Metal-catalyzed cross-coupling methodology to form carbon-carbon bonds has advanced organic synthesis. A., de Meijere, F. Diederich, Eds. *Metal-Catalyzed Cross-Coupling Reactions*, Vol. 2: Wiley-VCH, Weinheim, 2004. The Suzuki-Miyaura coupling is one of the preeminent methods for formation of carbon-carbon bonds and has been used in numerous synthetic ventures. N., Miyaura, *Topics in Current Chem.* 2002, 219, 11; and A. Suzuki, *Organomet. Chem.* 1999, 576, 147. In recent years, the palladium-catalyzed coupling of amines with aryl halides or sulfonates has been investigated. Muci, A. R.; Buchwald, S. L. *Top. Curr. Chem.* 2002, 219, 131; Yang, B. H.; Buchwald, S. L. *J. Organomet. Chem.* 1999, 576, 125; Hartwig, J. F. *Angew. Chem., Int. Ed.* 1998, 37, 2047. Unfortunately, these methods are still subject to undesirable limitations, notwithstanding the improvements in the substrate scope of palladium-catalyzed C—N bond-forming reactions realized by using weak bases, such as potassium phosphate or cesium carbonate. Old, D. W. et al. *J. Am. Chem. Soc.* 1998, 120, 9722; Wolfe, J. P.; Buchwald, S. L. *Tetrahedron Lett.* 1997, 38, 6359. Although the use of weak bases allows for the use of substrates containing ester, cyano, nitro and keto groups in the reaction, reactions of aryl substrates containing alcohol, phenol, or amide functional groups remain problematic. But see Harris, M. H. et al. *Org. Lett.* 2002, 4, 2885.

A new catalyst system that manifested high activity paired with extremely broad scope was recently reported. T. E. Barder, S. D. Walker, J. R. Martinelli, S. L. Buchwald, *J. Am. Chem. Soc.* 2005, 127, 4685; T. E. Barder, S. L. Buchwald *Org. Lett.* 2004, 6, 2649; S. D. Walker, T. E. Barder, J. R. Martinelli, S. L. Buchwald *Angew. Chem.* 2004, 116, 1907; and S. D. Walker, T. E. Barder, J. R. Martinelli, S. L. *Angew. Chem. Int. Ed.* 2004, 43, 1871. In addition, a catalyst system based on $PdCl_2(CH_3CN)_2/3$ which provides excellent reactivity in the copper-free Sonogashira coupling of aryl chlorides/tosylates and terminal alkynes has also been disclosed (for the structure of 3 see FIG. 1). D. Gelman, S. L. Buchwald *Angew. Chem.* 2003, 115, 6175; and D. Gelman, S. L. Buchwald *Angew. Chem. Int. Ed.* 2003, 42, 5993. However, this catalyst system was successful in coupling aryl alkynes only when the alkyne was added slowly over the course of the reaction. This fact is presumably due to competing non-productive oligomerization of the alkyne at higher concentrations in the presence of the catalyst.

There remains a need to develop reaction conditions for the coupling of water-soluble aryl chlorides and for the combination of difficult coupling partners in aqueous conditions. Additionally, compounds containing hydrophilic functional groups, which are insoluble in organic solvents and are present in many pharmaceutically interesting compounds, may be transformed using such a method, obviating the need for additional protection/deprotection steps. Further, conducting reactions in water is attractive since the aqueous components are easily separated from organic products. For reports of coupling reactions conducted in water or water/organic biphasic reaction solvents, see: C.-J. Li, T.-H. Chan. In *Organic Reactions in Aqueous Media*; Wiley: New York, 1997; *Organic Synthesis in Water*; P. A. Grieco, Ed.; Academic: Dordrecht, The Netherlands, 1997; *Aqueous-Phase Organometallic Catalysis*; B. Cornils, W. A. Herrmann, Eds., $2^{nd}$ ed.; Wiley-VCH: Weinheim, 2004; K. H. Shaughnessy, R. B. DeVasher *Curr. Org. Chem.* 2005, 9, 585; N. E. Leadbeater *Chem. Comm.* 2005, (Advanced Article); B. Liang, M. Dai, J. Chen, Z. Yang *J. Org. Chem.* 2005, 70, 391; G. Zhang Synlett 2005, 4, 619; M. S. Mohamed Ahmed, A. Mori *Tetrahedron* 2004, 60, 9977; C. Wolf, R. Lerebours *Org. Biomol. Chem.* 2004, 2, 2161; and S. Bhattacharya, S. Sengupta *Tetrahedron Lett.* 2004, 45, 8733.

Very few examples have been reported concerning palladium-catalyzed cross-coupling reactions of hydrophilic aryl chlorides with aryl boronic acids using purely aqueous reaction conditions. See, for example, a $NiCl_2$/dppe/trisulfonated triphenylphosphine system (J.-C. Galland, M. Savignac, J. P. Genet, *Tetrahedron Lett.* 1999, 40, 2323); using oxime-derived palladacycles (L. Botella, C. Najera, *Angew. Chem. Int. Ed.* 2002, 41, 179; and L. Botella Najera, *J. Organomet. Chem.* 2002, 663, 46); using di-2-pyridylmethylamine-based palladium complexes (C. Najera, J. Gil-Molto, S. Karlstrom, L. R. Falvello *Org. Lett.* 2003, 5, 1451); using palladium N-heterocyclic carbene complexes (I. Ozdemir, Y. Gok, N. Gurbuz, E. Cetinkaya, B. Cetinkaya *Heterat. Chem.* 2004, 15, 419; and I. Osdemir, S. Demir, S. Yaser, B. Cetinkaya, *Appl. Organomet. Chem.* 2005, 19, 55); or using TBAB-water mixtures (R. B. Bedford, M. E. Blake, C. P. Butts, D. Holder, *Chem. Comm.* 2003, 466). Several sulfonated phosphine derivatives have been prepared and used in cross-coupling reactions conducted in water or water/organic biphasic solvent systems. H. Gulyas, A. Szollosy, P. Szabo, P. Halmos, J. Bakos, *Eur. J. Org. Chem.* 2003, 2775; W. P. Mul, K. Ramkisoensing, P. C. J. Kamer, J. N. H. Reek, A. J. van der Linder, A. Marson, P. W. N. M. van Leeuwen, *Adv. Syn. Catal.* 2002, 344, 293; H. Gulyas, A. Szollosy, B. E. Hanson, J. Bakos, *Tetrahedron Lett.* 2002, 43, 2543; E. Schwab, S. Mecking, *Organometallics* 2001, 20, 5504; L. R. Moore, K. H. Shaughnessy *Org. Lett.* 2004, 6, 225; E. C. Western, J. R. Daft, E. M. Johnson II, P. M. Gannett, K. H. Shaughnessy, *J. Org. Chem.* 2003, 68, 6767; A. E. Sollewijn Gelpke, J. J. N. Veerman, M. S. Goedheijt, P. C. J. Kamer, P. W. N. M. van Leeuwen, H. Hiemstra *Tetrahedron* 1999, 55, 6657; H. Bahrmann, K. Bergrath, H.-J. Kleiner, P. Lappe, C. Naumann, D. Peters, D. Regnat, *J. Organomet. Chem.* 1996, 520, 97; J. P. Genet, A. Linguist, E. Blart, V. Mouries, M. Savignac, *Tetrahedron Lett.* 1995, 36, 1443. Shaughnessy reported that use of sterically demanding, water-soluble, alkylphosphine salts in the Suzuki-Miyaura, Sonogashira, and Heck coupling of unactivated aryl bromides provided excellent yields of products derived from carbon-carbon bond formation. R. B. DeVasher, L. R. Moore, K. H. Shaughnessy, *J. Org. Chem.* 2004, 69, 7919; and R. B. DeVasher, J. M. Spruell, D. A. Dixon, G. A. Broker, S. T. Griffin, R. D. Rogers, K. H. Shaughnessy, *Organometallics* 2005, 24, 962. Limitations to this methodology include a lengthy synthesis and poor thermal and air stability of the ligand. Furthermore, only a single example of a substituted aryl chloride was described. This was an activated aryl chloride (4-chlorobenzonitrile) that was combined with phenylboronic acid in a coupling that required 4 mol % of the palladium catalyst. Very recently, a Pd/glucosamine-based dicyclohexylarylphoshine catalyst was reported that displayed modest activity in Suzuki-Miyaura couplings of activated aryl chlorides when conducted in an water/toluene/ethanol solvent system. A. Konovets, A. Penciu, E. Framery, N. Percina, C. Goux-Henry, D. Sinou, *Tetrahedron Lett.* 2005, 46, 3205. This system was not reported to be general, and the ligand is difficult to prepare.

SUMMARY OF THE INVENTION

One aspect of the present invention relates to ligands for transition metals. A second aspect of the present invention relates to the use of catalysts comprising these ligands in various transition-metal-catalyzed carbon-heteroatom and carbon-carbon bond-forming reactions. The subject methods provide improvements in many features of the transition-metal-catalyzed reactions, including the range of suitable substrates, number of catalyst turnovers, reaction conditions, and efficiency. For example, improvements have been realized in transition metal-catalyzed: aryl amination reactions; aryl amidation reactions; Suzuki couplings; and Sonogashira couplings. In certain embodiments, the invention relates to catalysts and methods of using them that operate in aqueous solvent systems.

BRIEF DESCRIPTION OF THE FIGURES

FIG. 2 depicts Suzuki-Miyaura couplings of aryl chlorides using ligand 2. Reaction conditions: 1.0 equiv aryl chloride, 1.2 equiv boronic acid, 3.0 equiv $K_2CO_3$, degassed water (1.5 mL mmol$^{-1}$), cat. Pd(OAc)$_2$, ligand 2, L:Pd=2:1. [b] Yield of isolated product (average of 2 runs). [c] Conducted using microwave irradiation with cooling. [d] 4.0 equiv $K_2CO_3$ was used.

FIG. 3 depicts Suzuki-Miyaura couplings of water-soluble aryl chlorides using ligand 2. Reaction conditions: 1.0 equiv aryl chloride, 1.3-1.5 equiv boronic acid, 3.0 equiv $K_2CO_3$, degassed water (2.0 mL mmol$^{-1}$), Pd(OAc)$_2$ (1.0 mol %), ligand 2 (2.0 mol %), 100° C., 2-8 h. Reaction times and temperatures conducted were not optimized. [b] Yield of isolated product (average of 2 runs). [c] The reaction was conducted at 50° C. [d] The reaction was conducted using microwave irradiation with cooling, 150° C. for 10 min. [e] The reaction was conducted at 80° C. [f] The reaction was conducted at 80° C.

FIG. 4 depicts Suzuki-Miyaura couplings of heterocyclic halides using ligand 2. Reaction conditions: 1.0 equiv aryl halide, 1.3-1.5 equiv boronic acid, 3.0 equiv $K_2CO_3$, degassed water (4.0 mL mmol$^{-1}$), Pd(OAc)$_2$ (1.0 mol %), ligand 2 (2.0 mol %), 100° C., 10-12 h. Reaction times and temperatures were not optimized. [b] Yield of isolated product (average of 2 runs). [c] The reaction was conducted at 80° C. [d] The reaction was conducted using microwave irradiation with cooling, 150° C. for 10 min.

DETAILED DESCRIPTION OF THE INVENTION

Figure 1:
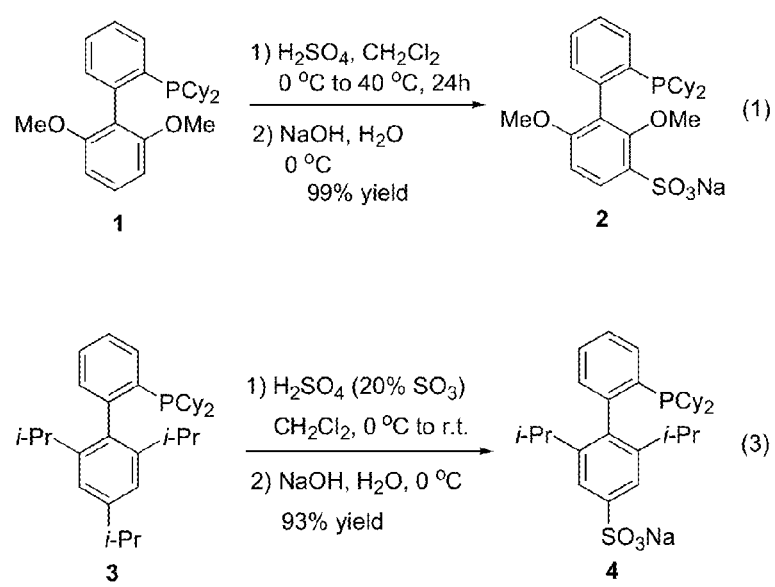
FIG. 1 depicts exemplary synthetic routes to water-soluble ligands 2 and 4.

One aspect of the present invention relates to ligands for transition metals. In certain embodiments, said ligands are soluble in water and aqueous solvent systems. A second aspect of the present invention relates to the use of catalysts comprising at least one of these ligands in various transition-metal-catalyzed carbon-heteroatom and carbon-carbon bond-forming reactions. In certain embodiments, said methods are conducted in water and aqueous solvent systems. The subject ligands and methods provide improvements in many features of the transition-metal-catalyzed reactions, including the range of suitable substrates, number of catalyst turnovers, reaction conditions, and efficiency. For example, remarkable improvements have been realized in transition metal-catalyzed Suzuki and Sonogashira couplings to give biaryl products.

Definitions

For convenience, before further description of the present invention, certain terms employed in the specification, examples, and appended claims are collected here.

The terms "biphenyl" and "binaphthylene" refer to the ring systems below. The numbers around the peripheries of the ring systems are the positional numbering systems used herein. Likewise, the capital letters contained within the individual rings of the ring systems are the ring descriptors used herein.

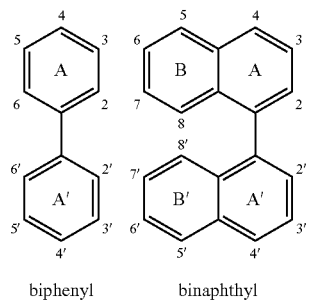

biphenyl    binaphthyl

The term "substrate aryl group" refers to an aryl group containing an electrophilic atom which is susceptible to the subject cross-coupling reaction, e.g., the electrophilic atom bears a leaving group. In reaction scheme 1, the substrate aryl is represented by ArX, and X is the leaving group. The aryl group, Ar, is said to be substituted if, in addition to X, it is substituted at yet other positions. The substrate aryl group can be a single ring molecule, or can be a component of a larger molecule.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The terms "electrophilic atom," "electrophilic center" and "reactive center" as used herein refer to the atom of the substrate aryl moiety which is attacked by, and forms a new bond to the nucleophilic heteroatom of the hydrazine and the like. In most (but not all) cases, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (s) constant. This well known constant is described in many references, for instance, J. March, *Advanced Organic Chemistry*, McGraw Hill Book Company, New York, (1977 edition) pp. 251-259. The Hammett constant values are generally negative for electron donating groups (s[P]=−0.66 for NH$_2$) and positive for electron withdrawing groups (s[P]=0.78 for a nitro group), s[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "reaction product" means a compound which results from the reaction of the hydrazine or the like and the substrate aryl group. In general, the term "reaction product" will be used herein to refer to a stable, isolable aryl ether adduct, and not to unstable intermediates or transition states.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

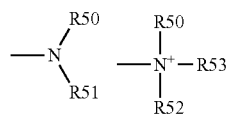

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

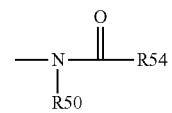

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

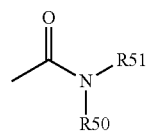

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

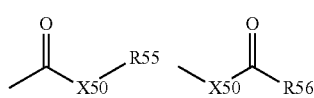

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

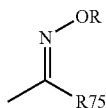

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkenyl, —O—(CH$_2$)$_m$—R61, where m and R61 are described above.

The term "sulfonate" is art recognized and refers to a moiety that may be represented by the general formula:

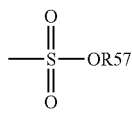

in which R57 is an electron pair, hydrogen, alkyl, cycloalkyl, or aryl.

The term "sulfate" is art recognized and includes a moiety that may be represented by the general formula:

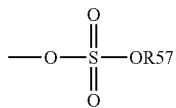

in which R57 is as defined above.

The term "sulfonamido" is art recognized and includes a moiety that may be represented by the general formula:

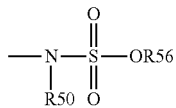

in which R50 and R56 are as defined above.

The term "sulfamoyl" is art-recognized and refers to a moiety that may be represented by the general formula:

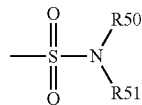

in which R50 and R51 are as defined above.

The term "sulfonyl" is art-recognized and refers to a moiety that may be represented by the general formula:

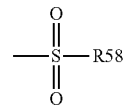

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

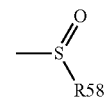

in which R58 is defined above.

The term "phosphoryl" is art-recognized and may in general be represented by the formula:

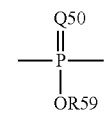

wherein Q50 represents S or O, and R59 represents hydrogen, a lower alkyl or an aryl. When used to substitute, e.g., an alkyl, the phosphoryl group of the phosphorylalkyl may be represented by the general formulas:

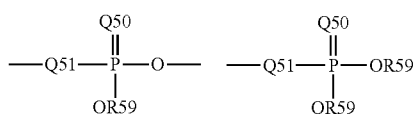

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

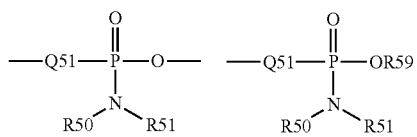

wherein Q51, R50, R51 and R59 are as defined above.

The term "phosphonamidite" is art-recognized and may be represented in the general formulas:

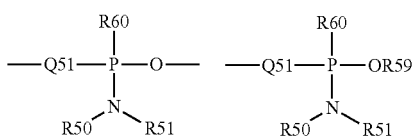

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991). Protected forms of the inventive compounds are included within the scope of this invention.

For purposes of this invention, the chemical elements are identified in accordance with the Periodic Table of the Elements, CAS version, *Handbook of Chemistry and Physics*, 67th Ed., 1986-87, inside cover.

A "polar solvent" means a solvent which has a dielectric constant ($\in$) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred polar solvents are DMF, DME, NMP, and acetonitrile.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

A "polar, aprotic solvent" means a polar solvent as defined above which has no available hydrogens to exchange with the compounds of this invention during reaction, for example DMF, acetonitrile, diglyme, DMSO, or THF.

A "hydroxylic solvent" means a solvent that comprises a hydroxyl moiety; for example, water, methanol, ethanol, tert-butanol, and ethylene glycol are hydroxylic solvents.

For purposes of this invention, the chemical elements are identified in accordance with the Periodic Table of the Elements, CAS version, Handbook of Chemistry and Physics, 67th Ed., 1986-87, inside cover.

Ligands of the Present Invention

In certain embodiments, a ligand of the present invention is represented by structure I:

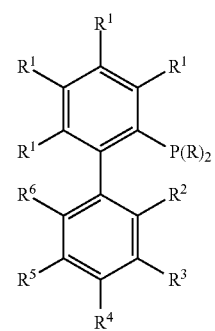

wherein

R is selected independently for each occurrence from the group consisting of alkyl, cycloalkyl, aryl, heteroaryl, aralkyl, heteroaralkyl, and —$(CH_2)_m$—$R^{80}$;

$R^1$ is selected independently for each occurrence from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^2$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^3$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^4$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^5$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^6$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^7$ is selected independently for each occurrence from the group consisting of —C(O)OM, —C(O)SM, —C(S)SM, —$C(NR^8)$OM, —$C(NR^8)$SM, —S(O)OM, —S(O)SM, —$S(O)_2$OM, —$S(O)_2$SM, —$P(O)(OM)_2$, —$P(O)(OR^8)$OM, —$P(O)(OR^8)NR^8$M, —$P(O)(OR^8)$SM, —$N(R^8)_3$M, —$P(R^8)_3$M, —$P(OR^8)_3$M and —$N(R^8)C(NR^8R^8)NR^8R^8$M;

$R^8$ is selected independently for each occurrence from the group consisting of hydrogen, alkyl, cycloalkyl, heterocycloalkyl, aryl, heteroaryl, aralkyl, and heteroaralkyl;

M is an alkali metal or an alkali earth metal;

$R^{80}$ represents an unsubstituted or substituted aryl, a cycloalkyl, a cycloalkenyl, a heterocycle, or a polycycle;

m is independently for each occurrence an integer in the range 0 to 8 inclusive;

provided that at least one of $R^3$, $R^4$ or $R^5$ is $R^7$; and the ligand is achiral or, when chiral, is a single stereoisomer or a mixture of stereoisomers.

In certain embodiments, the ligands of the present invention are represented by structure L and the attendant definitions, wherein R is selected independently for each occurrence from the group consisting of alkyl and cycloalkyl.

In certain embodiments, the ligands of the present invention are represented by structure L and the attendant definitions, wherein R is independently for each occurrence cycloalkyl.

In certain embodiments, the ligands of the present invention are represented by structure L and the attendant definitions, wherein R is cyclohexyl.

In certain embodiments, the ligands of the present invention are represented by structure L and the attendant definitions, wherein $R^1$ is hydrogen.

In certain embodiments, the ligands of the present invention are represented by structure L and the attendant definitions, wherein $R^2$ is alkyl or alkoxy.

In certain embodiments, the ligands of the present invention are represented by structure L and the attendant definitions, wherein $R^2$ is alkoxy.

In certain embodiments, the ligands of the present invention are represented by structure L and the attendant definitions, wherein $R^2$ is methoxy.

In certain embodiments, the ligands of the present invention are represented by structure L and the attendant definitions, wherein $R^2$ is alkyl.

In certain embodiments, the ligands of the present invention are represented by structure L and the attendant definitions, wherein $R^2$ is isopropyl.

In certain embodiments, the ligands of the present invention are represented by structure L and the attendant definitions, wherein $R^3$ is $R^7$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein $R^3$ is $R^7$; and $R^4$ and $R^5$ are hydrogen.

In certain embodiments, the ligands of the present invention are represented by structure L and the attendant definitions, wherein $R^3$ is —$S(O)_2$OM; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein $R^4$ is $R^7$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein $R^4$ is $R^7$; and $R^3$ and $R^5$ are hydrogen.

In certain embodiments, the ligands of the present invention are represented by structure L and the attendant definitions, wherein $R^4$ is —$S(O)_2$OM; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; and $R^1$ is hydrogen.

In certain embodiments, the ligands of the present invention are represented by structure L and the attendant definitions, wherein R is cyclohexyl; $R^1$ is hydrogen; and $R^2$ is alkyl or alkoxy.

In certain embodiments, the ligands of the present invention are represented by structure L and the attendant definitions, wherein R is cyclohexyl; $R^1$ is hydrogen; and $R^2$ is alkoxy.

In certain embodiments, the ligands of the present invention are represented by structure L and the attendant definitions, wherein R is cyclohexyl; $R^1$ is hydrogen; and $R^2$ is methoxy.

In certain embodiments, the ligands of the present invention are represented by structure L and the attendant definitions, wherein R is cyclohexyl; $R^1$ is hydrogen; and $R^2$ is alkyl.

In certain embodiments, the ligands of the present invention are represented by structure L and the attendant definitions, wherein R is cyclohexyl; $R^1$ is hydrogen; and $R^2$ is isopropyl.

In certain embodiments, the ligands of the present invention are represented by structure L and the attendant definitions, wherein R is cyclohexyl; $R^1$ is hydrogen; $R^3$ is $R^7$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^3$ is $R^7$; and $R^4$ and $R^5$ are hydrogen.

In certain embodiments, the ligands of the present invention are represented by structure L and the attendant definitions, wherein R is cyclohexyl; $R^1$ is hydrogen; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^4$ is $R^7$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^4$ is $R^7$; and $R^3$ and $R^5$ are hydrogen.

In certain embodiments, the ligands of the present invention are represented by structure L and the attendant definitions, wherein R is cyclohexyl; $R^1$ is hydrogen; $R^4$ is —$S(O)_2OM$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; and $R^2$ and $R^6$ are selected independently from the group consisting of hydrogen, alkyl and alkoxy.

In certain embodiments, the ligands of the present invention are represented by structure L and the attendant definitions, wherein R is cyclohexyl; $R^1$ is hydrogen; $R^2$ and $R^6$ are selected independently from the group consisting of hydrogen, alkyl and alkoxy; $R^3$ is $R^7$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^2$ and $R^6$ are selected independently from the group consisting of hydrogen, alkyl and alkoxy; $R^3$ is $R^7$; and $R^4$ and $R^5$ are hydrogen.

In certain embodiments, the ligands of the present invention are represented by structure L and the attendant definitions, wherein R is cyclohexyl; $R^1$ is hydrogen; $R^2$ and $R^6$ are selected independently from the group consisting of hydrogen, alkyl and alkoxy; $R^4$ is $R^7$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^2$ and $R^6$ are selected independently from the group consisting of hydrogen, alkyl and alkoxy; $R^4$ is $R^7$; and $R^3$ and $R^5$ are hydrogen.

In certain embodiments, the ligands of the present invention are represented by structure L and the attendant definitions, wherein R is cyclohexyl; $R^1$ is hydrogen; $R^2$ and $R^6$ are alkoxy; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^2$ and $R^6$ are alkyl; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^2$ and $R^6$ are alkoxy; $R^4$ is —$S(O)_2OM$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^2$ and $R^6$ are alkyl; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the ligands of the present invention are represented by structure L and the attendant definitions, wherein R is cyclohexyl; $R^1$ is hydrogen; $R^2$ and $R^6$ are methoxy; $R^3$ is —$S(O)_2ONa$; and $R^4$ and $R^5$ are hydrogen.

In certain embodiments, the ligands of the present invention are represented by structure L and the attendant definitions, wherein R is cyclohexyl; $R^1$ is hydrogen; $R^2$ and $R^6$ are methoxy; $R^3$ and $R^5$ are —$S(O)_2ONa$; and $R^4$ is hydrogen.

In certain embodiments, the ligands of the present invention are represented by structure L and the attendant definitions, wherein R is cyclohexyl; $R^1$ is hydrogen; $R^2$ and $R^6$ are isopropyl; $R^4$ is —$S(O)_2ONa$; and $R^3$ and $R^5$ are hydrogen.

Methods of the Present Invention

In certain embodiments, a method of the present invention is represented by Scheme 1:

Scheme 1

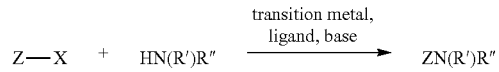

wherein

Z is selected from the group consisting of optionally substituted aryl, heteroaryl and alkenyl;

X is selected from the group consisting of Cl, Br, I, —OS(O)$_2$alkyl, and —OS(O)$_2$aryl;

R' and R" are selected, independently for each occurrence, from the group consisting of H, alkyl, heteroalkyl, aryl, formyl, acyl, alkoxycarbonyl, alkylaminocarbonyl, heteroaryl, aralkyl, alkoxyl, amino, trialkylsilyl, and triarylsilyl;

R' and R", taken together, may form an optionally substituted ring consisting of 3-10 backbone atoms inclusive; said ring optionally comprising one or more heteroatoms beyond the nitrogen to which R' and R" are bonded;

R' and/or R" may be covalently linked to Z;

the transition metal is selected from the Group 10 metals;

the base is selected from the group consisting of fluorides, hydrides, hydroxides, carbonates, phosphates, alkoxides, metal amides, and carbanions; and the ligand is selected from the group consisting of compounds represented by L:

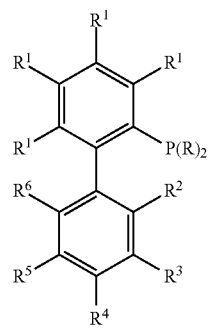

wherein

R is selected independently for each occurrence from the group consisting of alkyl, cycloalkyl, aryl, heteroaryl, aralkyl, heteroaralkyl, and —$(CH_2)_m$—$R^{80}$;

$R^1$ is selected independently for each occurrence from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^2$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^3$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^4$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^5$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^6$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^7$ is selected independently for each occurrence from the group consisting of —C(O)OM, —C(O)SM, —C(S)SM, —C(NR$^8$)OM, —C(NR$^8$)SM, —S(O)OM, —S(O)SM, —S(O)$_2$OM, —S(O)$_2$SM, —P(O)(OM)$_2$, —P(O)(OR$^8$)OM, —P(O)(OR$^8$)NR$^8$M, —P(O)(OR$^8$)SM, —N(R$^8$)$_3$M, —P(R$^8$)$_3$M, —P(OR$^8$)$_3$M and —N(R$^8$)C(NR$^8$R$^8$)NR$^8$R$^8$M;

$R^8$ is selected independently for each occurrence from the group consisting of hydrogen, alkyl, cycloalkyl, heterocycloalkyl, aryl, heteroaryl, aralkyl, and heteroaralkyl;

M is an alkali metal or an alkali earth metal;

$R^{80}$ represents an unsubstituted or substituted aryl, a cycloalkyl, a cycloalkenyl, a heterocycle, or a polycycle;

m is independently for each occurrence an integer in the range 0 to 8 inclusive;

provided that at least one of $R^3$, $R^4$ or $R^5$ is $R^7$; and the ligand when is achiral, or when chiral, is a single stereoisomer or a mixture of stereoisomers.

In certain embodiments, the present invention relates to the method represented by Scheme 1 and the attendant definitions, wherein the transition metal is palladium.

In certain embodiments, the present invention relates to the method represented by Scheme 1 and the attendant definitions, further comprising microwave irradiation.

In certain embodiments, a method of the present invention is represented by Scheme 2:

Scheme 2

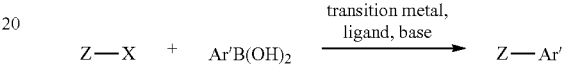

wherein

Z and Ar' are independently selected from the group consisting of optionally substituted aryl, heteroaryl and alkenyl;

X is selected from the group consisting of Cl, Br, I, —OS(O)$_2$alkyl, and —OS(O)$_2$aryl;

Z and Ar' may be covalently linked;

the transition metal is selected from the Group 10 metals;

the base is selected from the group consisting of fluorides, hydrides, hydroxides, carbonates, phosphates, alkoxides, metal amides, and carbanions; and the ligand is selected from the group consisting of compounds represented by L:

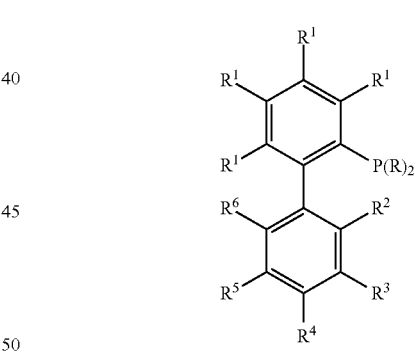

wherein

R is selected independently for each occurrence from the group consisting of alkyl, cycloalkyl, aryl, heteroaryl, aralkyl, heteroaralkyl, and —$(CH_2)_m$—$R^{80}$;

$R^1$ is selected independently for each occurrence from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^2$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$;

$R^3$ is selected from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, —$R^7$, and —$(CH_2)_m$—$R^{80}$;

$R^4$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, —R$^7$, and —(CH$_2$)$_m$—R$^{80}$;

$R^5$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, —R$^7$, and —(CH$_2$)$_m$—R$^{80}$;

$R^6$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, and —(CH$_2$)$_m$—R$^{80}$;

$R^7$ is selected independently for each occurrence from the group consisting of —C(O)OM, —C(O)SM, —C(S)SM, —C(NR$^8$)OM, —C(NR$^8$)SM, —S(O)OM, —S(O)SM, —S(O)$_2$OM, —S(O)$_2$SM, —P(O)(OM)$_2$, —P(O)(OR$^8$)OM, —P(O)(OR$^8$)NR$^8$M, —P(O)(OR$^8$)SM, —N(R$^8$)$_3$M, —P(R$^8$)$_3$M, —P(OR$^8$)$_3$M and —N(R$^8$)C(NR$^8$R$^8$)NR$^8$R$^8$M;

$R^8$ is selected independently for each occurrence from the group consisting of hydrogen, alkyl, cycloalkyl, heterocycloalkyl, aryl, heteroaryl, aralkyl, and heteroaralkyl;

M is an alkali metal or an alkali earth metal;

$R^{80}$ represents an unsubstituted or substituted aryl, a cycloalkyl, a cycloalkenyl, a heterocycle, or a polycycle;

m is independently for each occurrence an integer in the range 0 to 8 inclusive;

provided that at least one of $R^3$, $R^4$ or $R^5$ is $R^7$; and the ligand when is achiral, or when chiral, is a single stereoisomer or a mixture of stereoisomers.

In certain embodiments, the present invention relates to the method represented by Scheme 2 and the attendant definitions, wherein the transition metal is palladium.

In certain embodiments, the present invention relates to the method represented by Scheme 2 and the attendant definitions, wherein X is Cl, Br, or I.

In certain embodiments, the present invention relates to the method represented by Scheme 2 and the attendant definitions, wherein the base is potassium carbonate or cesium carbonate.

In certain embodiments, the present invention relates to the method represented by Scheme 2 and the attendant definitions, wherein the transition metal is palladium; and X is Cl, Br, or I.

In certain embodiments, the present invention relates to the method represented by Scheme 2 and the attendant definitions, wherein the transition metal is palladium; and the base is potassium carbonate or cesium carbonate.

In certain embodiments, the present invention relates to the method represented by Scheme 2 and the attendant definitions, wherein X is Cl, Br, or I; and the base is potassium carbonate or cesium carbonate.

In certain embodiments, the present invention relates to the method represented by Scheme 2 and the attendant definitions, wherein the transition metal is palladium; X is Cl, Br, or I; and the base is potassium carbonate or cesium carbonate.

In certain embodiments, the present invention relates to the method represented by Scheme 2 and the attendant definitions, further comprising microwave irradiation.

In certain embodiments, a method of the present invention is represented by Scheme 3:

Scheme 3

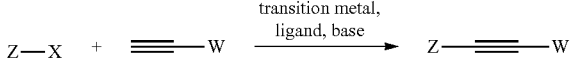

wherein

Z is selected from the group consisting of optionally substituted aryl, heteroaryl and alkenyl;

X is selected from the group consisting of Cl, Br, I, —OS(O)$_2$alkyl, and —OS(O)$_2$aryl;

W is selected from the group consisting of alkyl, —COOH, cycloalkyl, aryl, heteroaryl, aralkyl, heteroaralkyl, —(CH$_2$)$_m$—COOH, and —(CH$_2$)$_m$—R$^{80}$;

Z and W may be covalently linked;

the transition metal is selected from the Group 10 metals;

the base is selected from the group consisting of fluorides, hydrides, hydroxides, carbonates, phosphates, alkoxides, metal amides, and carbanions; and the ligand is selected from the group consisting of compounds represented by L:

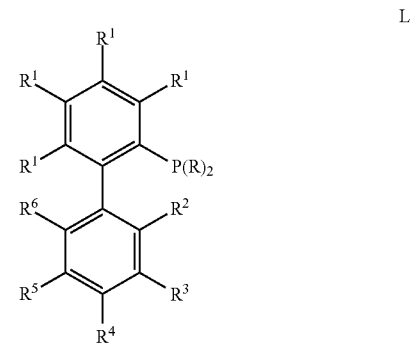

wherein

R is selected independently for each occurrence from the group consisting of alkyl, cycloalkyl, aryl, heteroaryl, aralkyl, heteroaralkyl, and —(CH$_2$)$_m$—R$^{80}$;

$R^1$ is selected independently for each occurrence from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, and —(CH$_2$)$_m$—R$^{80}$;

$R^2$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, and —(CH$_2$)$_m$—R$^{80}$;

$R^3$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, —R$^7$, and —(CH$_2$)$_m$—R$^{80}$;

$R^4$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, —R$^7$, and —(CH$_2$)$_m$—R$^{80}$;

$R^5$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, —R$^7$, and —(CH$_2$)$_m$—R$^{80}$;

$R^6$ is selected from the group consisting of hydrogen, halogen, alkyl, cycloalkyl, heterocycloalkyl, aryl, heteroaryl, aralkyl, heteroaralkyl, —OR$^8$, —N(R$^8$)$_2$, —Si(R$^8$)$_3$, and —(CH$_2$)$_m$—R$^{80}$;

$R^7$ is selected independently for each occurrence from the group consisting of —C(O)OM, —C(O)SM, —C(S)SM, —C(NR$^8$)OM, —C(NR$^8$)SM, —S(O)OM, —S(O)SM, —S(O)$_2$OM, —S(O)$_2$SM, —P(O)(OM)$_2$, —P(O)(OR$^8$)OM, —P(O)(OR$^8$)NR$^8$M, —P(O)(OR$^8$)SM, —N(R$^8$)$_3$M, —P(R$^8$)$_3$M, —P(OR$^8$)$_3$M and —N(R$^8$)C(NR$^8$R$^8$)NR$^8$R$^8$M;

$R^8$ is selected independently for each occurrence from the group consisting of hydrogen, alkyl, cycloalkyl, heterocycloalkyl, aryl, heteroaryl, aralkyl, and heteroaralkyl;

M is an alkali metal or an alkali earth metal;

$R^{80}$ represents an unsubstituted or substituted aryl, a cycloalkyl, a cycloalkenyl, a heterocycle, or a polycycle;

m is independently for each occurrence an integer in the range 0 to 8 inclusive;

provided that at least one of $R^3$, $R^4$ or $R^5$ is $R^7$; and the ligand when is achiral, or when chiral, is a single stereoisomer or a mixture of stereoisomers.

In certain embodiments, the present invention relates to the method represented by Scheme 3 and the attendant definitions, wherein the transition metal is palladium.

In certain embodiments, the present invention relates to the method represented by Scheme 3 and the attendant definitions, wherein X is Cl, Br, or I.

In certain embodiments, the present invention relates to the method represented by Scheme 3 and the attendant definitions, wherein the base is potassium carbonate or cesium carbonate.

In certain embodiments, the present invention relates to the method represented by Scheme 3 and the attendant definitions, wherein the transition metal is palladium; and X is Cl, Br, or I.

In certain embodiments, the present invention relates to the method represented by Scheme 3 and the attendant definitions, wherein the transition metal is palladium; and the base is potassium carbonate or cesium carbonate.

In certain embodiments, the present invention relates to the method represented by Scheme 3 and the attendant definitions, wherein X is Cl, Br, or I; and the base is potassium carbonate or cesium carbonate.

In certain embodiments, the present invention relates to the method represented by Scheme 3 and the attendant definitions, wherein the transition metal is palladium; X is Cl, Br, or I; and the base is potassium carbonate or cesium carbonate.

In certain embodiments, the present invention relates to the method represented by Scheme 3 and the attendant definitions, further comprising irradiating with microwave radiation.

In certain embodiments, the present invention relates to the method represented by Scheme 1, 2 or 3 and their attendant definitions, wherein R is selected independently for each occurrence from the group consisting of alkyl and cycloalkyl.

In certain embodiments, the present invention relates to the method represented by Scheme 1, 2 or 3 and their attendant definitions, wherein R is independently for each occurrence cycloalkyl.

In certain embodiments, the present invention relates to the method represented by Scheme 1, 2 or 3 and their attendant definitions, wherein R is cyclohexyl.

In certain embodiments, the present invention relates to the method represented by Scheme 1, 2 or 3 and their attendant definitions, wherein $R^1$ is hydrogen.

In certain embodiments, the present invention relates to the method represented by Scheme 1, 2 or 3 and their attendant definitions, wherein $R^2$ is alkyl or alkoxy.

In certain embodiments, the present invention relates to the method represented by Scheme 1, 2 or 3 and their attendant definitions, wherein $R^2$ is alkoxy.

In certain embodiments, the present invention relates to the method represented by Scheme 1, 2 or 3 and their attendant definitions, wherein $R^2$ is methoxy.

In certain embodiments, the present invention relates to the method represented by Scheme 1, 2 or 3 and their attendant definitions, wherein $R^2$ is alkyl.

In certain embodiments, the present invention relates to the method represented by Scheme 1, 2 or 3 and their attendant definitions, wherein $R^2$ is isopropyl.

In certain embodiments, the present invention relates to the method represented by Scheme 1, 2 or 3 and their attendant definitions, wherein $R^3$ is $R^7$; and $R^4$ and $R^5$ are selected independently from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$.

In certain embodiments, the present invention relates to the method represented by Scheme 1, 2 or 3 and their attendant definitions, wherein $R^3$ is $R^7$; and $R^4$ and $R^5$ are hydrogen.

In certain embodiments, the present invention relates to the method represented by Scheme 1, 2 or 3 and their attendant definitions, wherein $R^3$ is $-S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$.

In certain embodiments, the present invention relates to the method represented by Scheme 1, 2 or 3 and their attendant definitions, wherein $R^4$ is $R^7$; and $R^3$ and $R^5$ are selected independently from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$.

In certain embodiments, the present invention relates to the method represented by Scheme 1, 2 or 3 and their attendant definitions, wherein $R^4$ is $R^7$; and $R^3$ and $R^5$ are hydrogen.

In certain embodiments, the present invention relates to the method represented by Scheme 1, 2 or 3 and their attendant definitions, wherein $R^4$ is $-S(O)_2OM$; and $R^3$ and $R^5$ are selected independently from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$.

In certain embodiments, the present invention relates to the method represented by Scheme 1, 2 or 3 and their attendant definitions, wherein R is cyclohexyl; and $R^1$ is hydrogen.

In certain embodiments, the present invention relates to the method represented by Scheme 1, 2 or 3 and their attendant definitions, wherein R is cyclohexyl; $R^1$ is hydrogen; and $R^2$ is alkyl or alkoxy.

In certain embodiments, the present invention relates to the method represented by Scheme 1, 2 or 3 and their attendant definitions, wherein R is cyclohexyl; $R^1$ is hydrogen; and $R^2$ is alkoxy.

In certain embodiments, the present invention relates to the method represented by Scheme 1, 2 or 3 and their attendant definitions, wherein R is cyclohexyl; $R^1$ is hydrogen; and $R^2$ is methoxy.

In certain embodiments, the present invention relates to the method represented by Scheme 1, 2 or 3 and their attendant definitions, wherein R is cyclohexyl; $R^1$ is hydrogen; and $R^2$ is alkyl.

In certain embodiments, the present invention relates to the method represented by Scheme 1, 2 or 3 and their attendant definitions, wherein R is cyclohexyl; $R^1$ is hydrogen; and $R^2$ is isopropyl.

In certain embodiments, the present invention relates to the method represented by Scheme 1, 2 or 3 and their attendant definitions, wherein R is cyclohexyl; $R^1$ is hydrogen; $R^3$ is $R^7$; and $R^4$ and $R^5$ are selected independently from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$.

In certain embodiments, the present invention relates to the method represented by Scheme 1, 2 or 3 and their attendant definitions, wherein R is cyclohexyl; $R^1$ is hydrogen; $R^3$ is $R^7$; and $R^4$ and $R^5$ are hydrogen.

In certain embodiments, the present invention relates to the method represented by Scheme 1, 2 or 3 and their attendant definitions, wherein R is cyclohexyl; $R^1$ is hydrogen; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^4$ is $R^7$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^4$ is $R^7$; and $R^3$ and $R^5$ are hydrogen.

In certain embodiments, the present invention relates to the method represented by Scheme 1, 2 or 3 and their attendant definitions, wherein R is cyclohexyl; $R^1$ is hydrogen; $R^4$ is —$S(O)_2OM$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; and $R^2$ and $R^6$ are selected independently from the group consisting of hydrogen, alkyl and alkoxy.

In certain embodiments, the present invention relates to the method represented by Scheme 1, 2 or 3 and their attendant definitions, wherein R is cyclohexyl; $R^1$ is hydrogen; $R^2$ and $R^6$ are selected independently from the group consisting of hydrogen, alkyl and alkoxy; $R^3$ is $R^7$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^2$ and $R^6$ are selected independently from the group consisting of hydrogen, alkyl and alkoxy; $R^3$ is $R^7$; and $R^4$ and $R^5$ are hydrogen.

In certain embodiments, the present invention relates to the method represented by Scheme 1, 2 or 3 and their attendant definitions, wherein R is cyclohexyl; $R^1$ is hydrogen; $R^2$ and $R^6$ are selected independently from the group consisting of hydrogen, alkyl and alkoxy; $R^4$ is $R^7$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^2$ and $R^6$ are selected independently from the group consisting of hydrogen, alkyl and alkoxy; $R^4$ is $R^7$; and $R^3$ and $R^5$ are hydrogen.

In certain embodiments, the present invention relates to the method represented by Scheme 1, 2 or 3 and their attendant definitions, wherein R is cyclohexyl; $R^1$ is hydrogen; $R^2$ and $R^6$ are alkoxy; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^2$ and $R^6$ are alkyl; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^2$ and $R^6$ are alkoxy; $R^4$ is —$S(O)_2OM$; and $R^3$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^2$ and $R^6$ are alkyl; $R^3$ is —$S(O)_2OM$; and $R^4$ and $R^5$ are selected independently from the group consisting of hydrogen, halogen, alkyl, cycloalkyl, heterocycloalkyl, aryl, heteroaryl, aralkyl, heteroaralkyl, —$OR^8$, —$N(R^8)_2$, —$Si(R^8)_3$, and —$(CH_2)_m$—$R^{80}$.

In certain embodiments, the present invention relates to the method represented by Scheme 1, 2 or 3 and their attendant definitions, wherein R is cyclohexyl; $R^1$ is hydrogen; $R^2$ and $R^6$ are methoxy; $R^3$ is —$S(O)_2ONa$; and $R^4$ and $R^5$ are hydrogen.

In certain embodiments, the present invention relates to the method represented by Scheme 1, 2 or 3 and their attendant definitions, wherein R is cyclohexyl; $R^1$ is hydrogen; $R^2$ and $R^6$ are methoxy; $R^3$ and $R^5$ are —$S(O)_2ONa$; and $R^4$ is hydrogen.

In certain embodiments, the present invention relates to the method represented by Scheme 1, 2 or 3 and their attendant definitions, wherein R is cyclohexyl; $R^1$ is hydrogen; $R^2$ and $R^6$ are isopropyl; $R^4$ is —$S(O)_2ONa$; and $R^3$ and $R^5$ are hydrogen.

Various General Considerations

In certain embodiments of the reactions of the invention, there is no need to use large excesses of reactants, e.g., amine, amide, boronic acid, ketone and the like, or aromatic compound. The reactions proceed quickly and in high yield to the desired products using substantially stoichiometric amounts of reagents. For example, in the amination or amidation reactions of the invention, the amine or amide may be present in as little as a two-fold excess and preferably in no greater than a 20% excess relative to the aromatic compound. Alternatively, the aromatic compound may be present in as little as a two-fold excess and preferably in no greater than a 20% excess relative to the amine. An analogous discussion applies to the subject Suzuki couplings.

The reactions typically proceed at mild temperatures and pressures to give high yields of the product aryl amines, aryl amides, biaryls, and the like. Thus, yields of desired products greater than 45%, preferably greater than 75%, and even more preferably greater than 80%, may be obtained from reactions at mild temperatures according to the invention. The reaction may be carried out at temperature less than 150° C., and preferably in the range of 20-100° C. In certain certain embodiments, the reactions are carried out at ambient temperature.

The reactions can be run in a wide range of solvent systems, including polar aprotic solvents. Alternatively, in certain embodiments, the subject reactions may be carried in the absence of added solvent. In certain embodiments, the subject reaction may be carried out in a In certain embodiments, the subject reaction may be carried out in a polar solvent. In certain embodiments, the subject reaction may be carried out in an aprotic solvent. In certain embodiments, the subject reaction may be carried out in a polar, aprotic solvent. In certain embodiments, the subject reaction may be carried out in a hydroxylic solvent. In certain embodiments, the subject reaction may be carried out in water.

The ability to provide synthesis schemes for aryl amines, aryl amides, biaryls, and the like, which can be carried out under mild conditions and/or with non-polar solvents has broad application, especially in the agricultural and pharmaceutical industries, as well as in the polymer industry. In this regard, the subject reactions are particularly well-suited to reactants or products which include sensitive functionalities, e.g., which would otherwise be labile under harsh reaction conditions.

The subject amine arylation, amide arylation, Suzuki coupling, and the like can be used as part of combinatorial synthesis schemes to yield libraries of aryl amines, aryl amides, biaryls, and the like. Accordingly, another aspect of the present invention relates to use of the subject method to generate variegated libraries of aryl amines, aryl amides, biaryls, and the like, and to the libraries themselves. The libraries can be soluble or linked to insoluble supports, e.g., through a substituent of a reactant (prior to carrying out a reaction of the present invention), e.g., the aryl group, amine, amide, boronic acid, ketone, or the like, or through a substituent of a product (subsequent to carrying out a reaction of the present invention), e.g., the aryl amine, aryl amide, biaryl, or the like.

The ligands of the present invention and the methods based thereon enable the formation of carbon-heteroatom and carbon-carbon bonds—via transition metal catalyzed aminations, amidations, Suzuki couplings, Sonogashira couplings and the like—under conditions that would not yield appreciable amounts of the observed product(s) using ligands and methods known in the art. In certain embodiments, the ligands and methods of the present invention catalyze the aforementioned transformations at temperatures below 50° C., and in certain embodiments they occur at room temperature. When a reaction is said to occur under a given set of conditions it means that the rate of the reaction is such the bulk of the starting materials is consumed, or a significant amount of the desired product is produced, within 48 hours, and preferably within 24 hours, and most preferably within 12 hours. In certain embodiments, the ligands and methods of the present invention catalyze the aforementioned transformations utilizing less than 1 mol % of the catalyst complex relative to the limiting reagent, in certain embodiments less than 0.01 mol % of the catalyst complex relative to the limiting reagent, and in additional preferred embodiments less than 0.0001 mol % of the catalyst complex relative to the limiting reagent.

The ligands of the present invention and the methods based thereon can be used to produce synthetic intermediates that, after being subjected to additional methods known in the art, are transformed to desired end products, e.g., lead compounds in medicinal chemistry programs, pharmaceuticals, insecticides, antivirals and antifungals. Furthermore, the ligands of the present invention and the methods based thereon may be used to increase the efficiency of and/or shorten established routes to desired end products, e.g., lead compounds in medicinal chemistry programs, pharmaceuticals, insecticides, antivirals and antifungals.

Exemplary Catalyzed Reactions

As described above, one aspect of the present invention relates to novel ligands for transition metals. A second aspect of the present invention relates to the use of catalysts comprising these ligands in transition metal-catalyzed carbon-heteroatom and carbon-carbon bond-forming reactions. The subject methods provide improvements in many features of the transition metal-catalyzed reactions, including the range of suitable substrates, number of catalyst turnovers, reaction conditions, and efficiency. A preferred aspect of the present invention relates to a transition metal-catalyzed amination or amidation reaction which comprises combining an amine or amide with a substrate aryl group bearing an activated group X. The reaction includes at least a catalytic amount of a transition metal catalyst, comprising a novel ligand, and the combination is maintained under conditions appropriate for the metal catalyst to catalyze the arylation of the amine or amide.

Suitable substrate aryl compounds include compounds derived from simple aromatic rings (single or polycylic) such as benzene, naphthalene, anthracene and phenanthrene; or heteroaromatic rings (single or polycyclic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine and the like. In preferred embodiment, the reactive group, X, is substituted on a five, six or seven membered ring (though it can be part of a larger polycycle).

In certain embodiments, the aryl substrate may be selected from the group consisting of phenyl and phenyl derivatives, heteroaromatic compounds, polycyclic aromatic and heteroaromatic compounds, and functionalized derivatives thereof. Suitable aromatic compounds derived from simple aromatic rings and heteroaromatic rings, include but are not limited to, pyridine, imidizole, quinoline, furan, pyrrole, thiophene, and the like. Suitable aromatic compounds derived from fused ring systems, include but are not limited to naphthalene, anthracene, tetralin, indole and the like.

Suitable aromatic compounds may have the formula $Z_p\text{ArX}$, where X is an activated substituent. An activated substituent, X, is characterized as being a good leaving group. In general, the leaving group is a group such as a halide or sulfonate. Suitable activated substituents include, by way of example only, halides such as chloride, bromide and iodide, and sulfonate esters such as triflate, mesylate, nonaflate and tosylate. In certain embodiments, the leaving group is a halide selected from iodine, bromine, and chlorine.

Z represents one or more optional substituents on the aromatic ring, though each occurrence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, —$(CH_2)_m$—$R_{80}$, —$(CH_2)_m$—OH, —$(CH_2)_m$—O-lower alkyl, —$(CH_2)_m$—O-lower alkenyl, —$(CH_2)_m$—O—$(CH2)_n$-$R_{80}$, —$(CH_2)_m$ —SH, —(CH$_2$)$_m$—S-lower alkyl, —(CH$_2$)$_m$—S-lower alkenyl, —(CH$_2$)$_m$—S—(CH$_2$)$_n$—R$_{80}$, or protecting groups of the above or a solid or polymeric support; R$_{80}$ represents a substituted or unsubstituted aryl, aralkyl, cycloalkyl, cycloalkenyl, or heterocycle; and n and m are independently for each occurrence zero or an integer in the range of 1 to 6. P is preferably in the range of 0 to 5. For fused rings, where the number of substitution sites on the aryl group increases, p may be adjusted appropriately.

In certain embodiments, suitable substituents Z include alkyl, aryl, acyl, heteroaryl, amino, carboxylic ester, carboxylic acid, hydrogen, ether, thioether, amide, carboxamide, nitro, phosphonic acid, hydroxyl, sulfonic acid, halide, pseudohalide groups, and substituted derivatives thereof, and p is in the range of 0 to 5. In particular, the reaction is anticipated to be compatible with acetals, amides and silyl ethers. For fused rings, where the number of substitution sites on the aromatic ring increases, p may be adjusted appropriately.

A wide variety of substrate aryl groups are useful in the methods of the present invention. The choice of substrate will depend on factors such as the amine, boronic acid, ketone, or the like to be employed and the desired product, and an appropriate aryl substrate will be made apparent to the skilled artisan by these teachings. It will be understood that the aryl substrate preferably will not contain any interfering functionalities. It will further be understood that not all activated aryl substrates will react with every amine, boronic acid, ketone, or the like.

The reactive the amine, amide, boronic acid, or the like can be a molecule separate from the substrate aryl group, or a substituent of the same molecule (e.g., for intramolecular variations).

The amine, amide, boronic acid, or the like is selected to provide the desired reaction product. The amine, boronic acid, or the like may be functionalized. The amine, boronic acid, or the like may be selected from a wide variety of structural types, including but not limited to, acyclic, cyclic or heterocyclic compounds, fused ring compounds or phenol derivatives. The aromatic compound and the amine, boronic acid, or the like may be included as moieties of a single molecule, whereby the arylation reaction proceeds as an intramolecular reaction.

In certain embodiments, the amine, amide, boronic acid, or the like is generated in situ by conversion of a precursor under the reaction conditions.

In certain embodiments, the aryl substrate and/or the amine, amide, boronic acid, or the ligand is attached, either directly or via a tether, to a solid support.

Alternatively, the corresponding salt of the amine, amide, boronic acid, or the like, may be prepared and used in place of the amine, amide, boronic acid, or the like. When the corresponding salt of the amine, amide, boronic acid, or the like is used in the reaction, an additional base may not be required.

The active form of the transition metal catalyst is not well characterized. Therefore, it is contemplated that the "transition metal catalyst" of the present invention, as that term is used herein, shall include any catalytic transition metal and/or catalyst precursor as it is introduced into the reaction vessel and which is, if necessary, converted in situ into the active form, as well as the active form of the catalyst which participates in the reaction.

In certain embodiments, the transition metal catalyst complex is provided in the reaction mixture is a catalytic amount. In certain embodiments, that amount is in the range of 0.0001 to 20 mol %, and preferably 0.05 to 5 mol %, and most preferably 1-4 mol %, with respect to the limiting reagent, which may be either the aromatic compound the amine, boronic acid, ketone, or the like (or the corresponding salt thereof), depending upon which reagent is in stoichiometric excess. In the instance where the molecular formula of the catalyst complex includes more than one metal, the amount of the catalyst complex used in the reaction may be adjusted accordingly. By way of example, Pd$_2$(dba)$_3$ has two metal centers; and thus the molar amount of Pd$_2$(dba)$_3$ used in the reaction may be halved without sacrificing catalytic activity.

Catalysts containing palladium and nickel are preferred. It is expected that these catalysts will perform similarly because they are known to undergo similar reactions, namely oxidative-addition reactions and reductive-elimination reactions, which are thought to be involved in the formation of the products of the present invention. The novel ligands are thought to modify the catalyst performance by, for example, modifying reactivity and preventing undesirable side reactions.

As suitable, the catalysts employed in the subject method involve the use of metals which can mediate cross-coupling of the aryl groups ArX and the amine, boronic acid, ketone, or the like as defined above. In general, any transition metal (e.g., having d electrons) may be used to form the catalyst, e.g., a metal selected from one of Groups 3-12 of the periodic table or from the lanthanide series. However, in certain embodiments, the metal will be selected from the group of late transition metals, e.g. preferably from Groups 5-12 and even more preferably Groups 7-11. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst should be a zero valent transition metal, such as Pd or Ni with the ability to undergo oxidative addition to Ar—X bond. The zero-valent state, M(0), may be generated in situ, e.g., from M(II).

To further illustrate, suitable transition metal catalysts include soluble or insoluble complexes of platinum, palladium and nickel. Nickel and palladium are particularly preferred and palladium is most preferred. A zero-valent metal center is presumed to participate in the catalytic carbon-heteroatom or carbon-carbon bond forming sequence. Thus, the metal center is desirably in the zero-valent state or is capable of being reduced to metal(0). Suitable soluble palladium complexes include, but are not limited to, tris(dibenzylideneacetone)dipalladium [Pd$_2$(dba)$_3$], bis(dibenzylideneacetone) palladium [Pd(dba)$_2$] and palladium acetate. Alternatively, particularly for nickel catalysts, the active species for the oxidative-addition step may be in the metal (+1) oxidation state.

Catalysts containing palladium and nickel are preferred. It is expected that these catalysts will perform comparably because they are known in the art to undergo similar reactions, namely cross-coupling reactions, which may be involved in the formation of the products of the present invention, e.g., arylamines, diaryls, α-arylketones, or the like.

The coupling can be catalyzed by a palladium catalyst which palladium may be provided in the form of, for illustrative purposes only, Pd/C, PdCl$_2$, Pd(OAc)$_2$, (CH$_3$CN)$_2$PdCl$_2$, Pd[P(C$_6$H$_5$)$_3$]$_4$, and polymer supported Pd(0). In other embodiments, the reaction can be catalyzed by a nickel catalyst which nickel may be provided in the form of, for illustrative purposes only, Ni(acac)$_2$, NiCl$_2$[P(C$_6$H$_5$)]$_2$, Ni(1,5-cyclooctadiene)$_2$, Ni(1,10-phenanthroline)$_2$, Ni(dppf)$_2$, NiCl$_2$(dppf), NiCl$_2$(1,10-phenanthroline), Raney nickel and the like, wherein "acac" represents acetylacetonate.

The catalyst will preferably be provided in the reaction mixture as metal-ligand complex comprising a bound supporting ligand, that is, a metal-supporting ligand complex. The ligand effects can be key to favoring, inter alia, the reductive elimination pathway or the like which produces the products, rather than side reactions such as β-hydride elimination. In certain embodiments, the subject reaction employs bidentate ligands such as bisphosphines or aminophosphines. The ligand, if chiral can be provided as a racemic mixture or a purified stereoisomer. In certain instances, e.g. the improved method for the synthesis of aryl amines, the use of a racemic, chelating ligand is preferred.

The ligand, as described in greater detail below, may be a chelating ligand, such as by way of example only, alkyl and aryl derivatives of phosphines and bisphosphines, amines, diamines, imines, arsines, and hybrids thereof, including hybrids of phosphines with amines. Weakly or non-nucleophilic stabilizing ions are preferred to avoid undesired side reactions involving the counter ion. The catalyst complex may include additional ligands as required to obtain a stable complex. Moreover, the ligand can be added to the reaction mixture in the form of a metal complex, or added as a separate reagent relative to the addition of the metal.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalytic metal center. In some preferred embodiments, the supporting ligand is a chelating ligand. Although not bound by any theory of operation, it is hypothesized that the supporting ligands suppress unwanted side reactions as well as enhance the rate and efficiency of the desired processes. Additionally, they typically prevent precipitation of the catalytic transition metal. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol % relative to the limiting reagent, i.e., amine, boronic acid, ketone or the like, or aromatic compound. The ratio of the supporting ligand to catalyst complex is typically in the range of about 1 to 20, and preferably in the range of about 1 to 4 and most preferably 2. These ratios are based upon a single metal complex and a single binding site ligand. In instances where the ligand contains additional binding sites (i.e., a chelating ligand) or the catalyst contains more than one metal, the ratio is adjusted accordingly. By way of example only, the supporting ligand BINAP contains two coordinating phosphorus atoms and thus the ratio of BINAP to catalyst is adjusted downward to about 1 to 10, preferably about 1 to 2 and most preferably 1. Conversely, $Pd_2(dba)_3$ contains two palladium metal centers and the ratio of a non-chelating ligand to $Pd_2(dba)_3$ is adjusted upward to 1 to 40, preferably 1 to 8 and most preferably 4.

In certain embodiments of the subject method, the transition metal catalyst includes one or more phosphine or aminophosphine ligands, e.g., as a Lewis basic ligand that controls the stability and electron transfer properties of the transition metal catalyst, and/or stabilizes the metal intermediates. Phosphine ligands are commercially available or can be prepared by methods similar to known processes. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(dicyclohexylphosphino)ethane, 1,3-bis(dicyclohexylphosphino)propane, 1,3-bis(diisopropylphosphino)propane, 1,4-bis(diisopropylphosphino)-butane and 2,4-bis(dicyclohexylphosphino)pentane. The aminophosphines may be monodentate, e.g. each molecule of aminophosphine donates to the catalytic metal atom only a Lewis basic nitrogen atom or a Lewis basic phosphorus atom. Alternatively, the aminophosphine may be a chelating ligand, e.g. capable of donating to the catalytic metal atom both a Lewis basic nitrogen atom and a Lewis basic phosphorus atom.

In some instances, it may be necessary to include additional reagents in the reaction mixture to promote reactivity of either the transition metal catalyst or activated aryl nucleus. In particular, it may be advantageous to include a suitable base. In general, a variety of bases may be used in practice of the present invention. It has not been determined at which point(s) in the mechanisms of the subject transformations the base participates. The base may optionally be sterically hindered to discourage metal coordination of the base in those circumstances where such coordination is possible, i.e., alkali metal alkoxides. Exemplary bases include such as, by way of example only: alkoxides such as sodium tert-butoxide; alkali metal amides such as sodium amide, lithium diisopropylamide, and alkali metal bis(trialkylsilyl)amide, e.g., such as lithium bis(trimethylsilyl)amide (LiHMDS) or sodium bis(trimethylsilyl)amide (NaHMDS); tertiary amines (e.g. triethylamine, trimethylamine, 4-(dimethylamino)pyridine (DMAP), 1,5-diazabicycl[4.3.0]non-5-ene (DBN), 1,5-diazabicyclo[5.4.0]undec-5-ene (DBU); alkali or alkaline earth carbonate, bicarbonate or hydroxide (e.g. sodium, magnesium, calcium, barium, potassium carbonate, phosphate, hydroxide and bicarbonate). By way of example only, suitable bases include NaH, LiH, KH, $K_2CO_3$, $Na_2CO_3$, $Tl_2CO_3$, $Cs_2CO_3$, K(OtBu), Li(OtBu), Na(OtBu) K(OAr), Na(OAr), and triethylamine, or mixtures thereof. Preferred bases include CsF, $K_3PO_4$, DBU, NaOt-Bu, KOt-Bu, $LiN(i-Pr)_2$ (LDA), $KN(SiMe_3)_2$, $NaN(SiMe_3)_2$, and $LiN(SiMe_3)_2$.

Base is used in approximately stoichiometric proportions in the subject methods. The present invention has demonstrated that there is no need for large excesses of base in order to obtain good yields of the desired products under mild reaction conditions. No more than four equivalents of base, and preferably no more than two equivalents, are needed. Furthermore, in reactions using the corresponding salt of an amine, boronic acid or the like, additional base may not be required.

As is clear from the above discussion, the products which may be produced by the amination, Suzuki coupling, and α-arylation reactions of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrile reduction, acylation of alcohols by esters, acylation of amines and the like.

Exemplary Suzuki-Miyaura Couplings

Ligand Selection. It has been shown that the electron-rich lower aromatic ring of 1 is readily amenable to the incorporation of a water-solublizing group, such as a sulfonate (see FIG. 1 for structure of 1). In fact, treatment of 1 with concentrated $H_2SO_4$ at 40° C. for 24 h gave 2 with exclusive monosulfonation at the 3'-position in 99% yield after treatment with NaOH and workup (FIG. 1, Equation 1). Utilizing 2, excellent yields were obtained in Suzuki-Miyaura couplings of highly functionalized aryl chlorides and heterocyclic chlorides/bromides (containing carboxylic acids, amines, alcohols, sulfonamides and sulfonic acids) and aryl/alkyl-boronic acids in aqueous media.

Selected Reactions. Using a catalyst system based on 2, the coupling of hydrophobic and hydrophilic substrates was investigated; initial results are shown in FIG. 2. The coupling of electronically neutral 1-chloro-3,4-dimethylbenzene and phenylboronic acid at room temperature using water as the solvent provided the corresponding biaryl in 99% yield (FIG. 2, entry 1). A temperature of 100° C. was necessary for successful coupling of 3-chlorobenzamide and hindered 2,6-dimethylphenylboronic acid resulting in 99% yield of the biaryl amide (FIG. 2, entry 2). Using microwave irradiation (150° C.), the same coupling product was obtained in 94% yield in 10 minutes (FIG. 2, entry 2). This result indicates that the catalyst system based on 2 exhibits high thermal stability. It was found that coupling of 3-chlorobenzoic acid with phenylboronic acid proceeds at room temperature using 0.5% Pd and at 100° C. using 0.1% Pd, providing the coupled product in 97% yield for both cases (FIG. 2, entry 3). Similar catalytic activity was observed in the coupling of 3-chlorobenzoic acid and 2-methylphenylboronic acid using 0.5% Pd at room temperature and 0.1% Pd at 100° C. giving the desired product in 95% and 96% yield, respectively (FIG. 2, entry 4). Using microwave irradiation (150° C.) and 0.1% Pd, the same coupling product was obtained in 98% yield in 10 minutes (FIG. 2, entry 4). The combination of 5-chloro-2-hydroxybenzoic acid and 2-methylphenylboronic acid, while slower, provided an excellent yield of the biaryl product at 2% Pd (r.t.) or 0.1% Pd (100° C.) (FIG. 2, entry 5).

The Suzuki-Miyaura coupling of hydrophobic aryl bromides in aqueous media has been reported to occur with an assortment of catalysts including those that operate without a supporting ligand. Successful application to moderately hindered substrate combinations, however, have not been disclosed or possible. To ascertain whether or not a Pd(OAc)$_2$/2 catalyst system could address this limitation, two reasonably hindered substrate combinations were examined using water as the solvent at room temperature: the reaction of 2-bromomesitylene with 2-methylphenylboronic acid and 2-bromotoluene with 2,6-dimethylphenylboronic acid to form a biaryl that contains three substituents ortho to the aryl-aryl connection (FIG. 2, entries 6-7). Attempts to effect the coupling of 2-bromomesitylene with 2,6-dimethylphenylboronic acid in water at 100° C., to form a biaryl with four substituents ortho to the aryl-aryl connection provided none of the desired product. This is in contrast to what is observed with a catalytic system using 1. To our knowledge, this represents the first successful coupling of a hindered substrate combination conducted using a water or water/organic biphasic solvent at room temperature.

To determine the scope of this process, the reaction of chlorobenzoic acids with 3-carboxyphenylboronic acid, 2-hydroxyphenylboronic acid, 2-aminophenylboronic acid, 2-acetylphenylboronic acid and 2-formylphenylboronic acid were examined; these coupling processes all proceeded in excellent yield (FIG. 3, entries 1-3) using 1% catalyst. Using microwave irradiation (150° C.), 4-chlorobenzoic acid and 3-carboxyphenylboronic acid were coupled in 10 minutes with 1% Pd providing the product in 95% yield (FIG. 3, entry 1), again demonstrating catalyst stability at higher temperatures.

Suzuki-Miyaura couplings of functionalized hydrophilic aryl chlorides and substituted arylboronic acids are also possible. Chlorobenzoic acids containing phenolic (FIG. 3, entry 4) and amino (FIG. 3, entry 5) groups on the aromatic ring were effectively coupled with substituted arylboronic acids (4-cyanophenylboronic acid and 3-aminophenylboronic acid, respectively) generating the biaryl products in high yields (92% and 99%, respectively). Of interest, 4-chlorobenzenesulfonic acid successfully coupled with methylboronic acid giving the sulfonic acid derivative in 96% yield, (FIG. 3, entry 6). Remarkably, this is a Suzuki-Miyaura coupling of an arylhalide bearing an unprotected sulfonic acid. The sulfonic acid is undoubtedly rapidly transformed to the sulfonate under the reaction conditions. For examples of Suzuki-Miyaura couplings of aryl halides with protected sulfonic acids: a) B. G. Avitabile, C. A. Smith, D. B. Judd *Org. Lett.* 2005, 7, 843. b) A. Hari, B. L. Miller, *Org. Lett.* 1999, 1, 2109. c) E. W. Baxter, J. K. Rueter, S. O, Nortey, A. B. Reitz, *Tetrahedron Lett.* 1998, 39, 979.

It is well known that applications of heterocyclic compounds (which are commonplace in numerous natural products) in cross-coupling processes remain a challenge. Very few examples of aqueous-phase Suzuki couplings of water-soluble heterocyclic halides have been published. The use of 2 as a supporting ligand in the Suzuki-Miyaura coupling with a variety of challenging hydrophilic heterocyclic halides has been examined; results are shown in FIG. 4. As is shown, the method works well for a number of different carboxylic acid containing heterocyclic chlorides and bromides including indole (possessing a free N—H), pyridine and thiophene (FIG. 4, entries 2-3, 5). Even 2-amino-5-chloropyridine, which can potentially chelate to metal centers such as Pd(II), is successfully coupled with 3-pyridylboronic acid in 93% yield (FIG. 4, entry 4).

Figure 5:
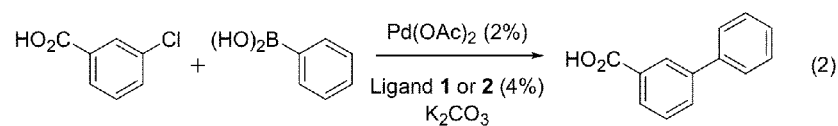
FIG. 5 depicts screening of conditions for Suzuki-Miyaura Coupling with ligands 1 and 2. Reaction conditions: 1.0 equiv aryl chloride, 1.2 equiv boronic acid, 3.0 equiv $K_2CO_3$, solvent (2.0 mL mmol$^{-1}$), cat. Pd(OAc)$_2$, ligand 1 or 2, L:Pd=2:1, 14 h. [b] NMR yield of product. [c] The reaction was complete in 2 h.

The Suzuki-Miyaura coupling of 3-chlorobenzoic acid and phenylboronic acid employing 1 provided efficient conversion and yield of the desired product using an water/organic biphasic solvent system at 100° C. (FIG. 5, entries 3 and 4). However at room temperature, under these conditions, the reaction was sluggish (FIG. 5, entry 5). A dramatic increase in activity was observed when using the amphiphilic ligand 2, as compared to 1, in water at room temperature providing the biaryl product in 97% yield (FIG. 5, entry 7). Although a catalyst system using 1 in a similar biphasic solvent system may work in many instances, this has not yet been explored.

Exemplary Sonogashira Couplings

Ligand Selection. Incorporating a water-solubilizing sulfonate group on 3 provides an amphiphilic Sonogashira catalyst which can be used to address the limitations that were previously reported and allow for the coupling of hydrophilic substrate combinations (see FIG. 1 for the structure of 3). It was found that treatment of 3 with fuming sulfuric acid ($H_2SO_4$/20% $SO_3$) at room temperature for 24 h provided 4, with selective mono-sulfonation at the 4'-position, in 93% yield after treatment with NaOH and workup (FIG. 1, Equation 3).

Figure 6:
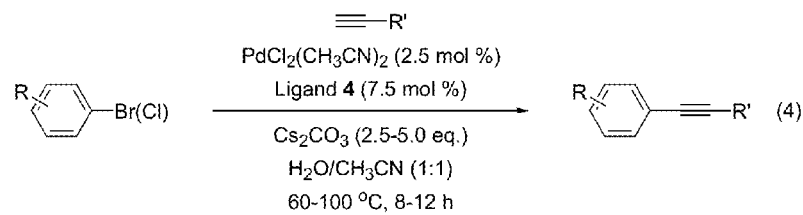
FIG. 6 depicts Sonogashira coupling of aryl halides using ligand 4. Reaction conditions: 1.0 equiv aryl halide, 1.3 equiv terminal alkyne, 2.5-5.0 equiv $Cs_2CO_3$, degassed water (2.0 mL mmol$^{-1}$), $CH_3CN$ (2.0 mL mmol$^{-1}$), PdCl$_2$(CH$_3$CN)$_2$ (2.5 mol %), ligand 4 (7.5 mol %), 100° C., 8-12 h. Reaction times were not optimized. [b] Yield of isolated product (average of 2 runs). [c] The alkyne was added to the reaction at 0° C. and heated to 60° C. [d] To ease in purification, the product was converted to the methyl ester using trimethylsilyldiazomethane.

Selected Reactions. For the first time, using a catalyst system based on PdCl$_2$(CH$_3$CN)$_2$/4 and a water/acetonitrile biphasic solvent system, propiolic acid was successfully coupled with 3-bromoanisole and 3-bromobenzoic acid providing 70% and 69% yields of aryl alkynoic acids, respectively (FIG. 6, entries 1-2). This result represents a significant advancement in Sonogashira coupling reactions, since electron-deficient propiolate esters have been problematic coupling partners due to their increased reactivity towards nucleophilic attack and their propensity to polymerize in the presence of Pd catalysts. See, for example, the use of electron-deficient zinc acetylides allows coupling with aryl halides (E.-I. Negishi, L. Anastasia *Chem. Rev.* 2003, 103, 1979 and references within); the use of $K_2CO_3$ for the coupling of electron-deficient terminal alkynes and electron-deficient or neutral aryl iodides (T. Eckert, J. Ipaktschi *Syn. Comm.* 1998, 28, 327); or the use of $K_2CO_3$ for the coupling of electron-deficient terminal alkynes and diphenyliodonum salts (U. Radhakrishnan, P. J. Stang *Org. Lett.* 2001, 3, 859). Interestingly, water was essential to the coupling reaction of aryl iodides and various alkynoates. Y. Uozumi, Y. Kobayashi *Heterocycles* 2003, 59, 71. Good yields were obtained for the coupling of hydrophilic aryl chlorides bearing carboxylic acids (FIG. 6, entries 3 and 5) and an alkyne containing an aliphatic carboxylic acid (FIG. 6, entry 4). Further, use of 4 and a water/acetonitrile solvent system, the coupling of aryl chlorides and aryl alkynes proceeds obviating the need to employ slow addition of the aryl alkyne (FIG. 6, entries 6-8). This result may be attributed to the lower effective concentration of the alkyne in proximity to the catalyst, which resides at the water/organic interface.

Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran, water and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants or a ligand anchored to a solid support.

In certain embodiments it is preferable to perform the reactions under an inert atmosphere of a gas such as nitrogen or argon.

In certain embodiments it is preferable to perform the reactions under microwave irradiation. The term "microwave" refers to that portion of the electromagnetic spectrum between about 300 and 300,000 megahertz (MHz) with wavelengths of between about one millimeter (1 mm) and one meter (1 m). These are, of course, arbitrary boundaries, but help quantify microwaves as falling below the frequencies of infrared radiation but above those referred to as radio frequencies. Similarly, given the well-established inverse relationship between frequency and wavelength, microwaves have longer wavelengths than infrared radiation, but shorter than radio frequency wavelengths. Microwave-assisted chemistry techniques are generally well established in the academic and commercial arenas. Microwaves have some significant advantages in heating certain substances. In particular, when microwaves interact with substances with which they can couple, most typically polar molecules or ionic species, the microwaves can immediately create a large amount of kinetic energy in such species which provides sufficient energy to initiate or accelerate various chemical reactions. Microwaves also have an advantage over conduction heating in that the surroundings do not need to be heated because the microwaves can react instantaneously with the desired species.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion. In a order of events that, in some cases, can lead to an enhancement of the reaction rate, the base, e.g. t-BuONa, is the last ingredient to be added to the reaction mixture.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivatization with one or more of substituents of the aryl group.

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

Direct Characterization. A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

Multipin Synthesis. The libraries of the subject method can take the multipin library format. Briefly, Geysen and coworkers (Geysen et al. (1984) PNAS 81:3998-4002) introduced a method for generating compound libraries by a parallel synthesis on polyacrylic acid-grated polyethylene pins arrayed in the microtiter plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811-5814; Valerio et al. (1991) Anal Biochem 197:168-177; Bray et al. (1991) Tetrahedron Lett 32:6163-6166).

Divide-Couple-Recombine. In yet another embodiment, a variegated library of compounds can be provided on a set of beads utilizing the strategy of divide-couple-recombine (see, e.g., Houghten (1985) PNAS 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

Combinatorial Libraries by Light-Directed, Spatially Addressable Parallel Chemical Synthesis. A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271-280; Fodor, S. P. A. (1991) Science 251:767; Pirrung et al. (1992) U.S. Pat. No. 5,143,854; Jacobs et al. (1994) Trends Biotechnol 12:19-26). The spatial resolution of photolithography affords miniaturization. This technique can be carried out through the use protection/deprotection reactions with photolabile protecting groups.

The key points of this technology are illustrated in Gallop et al. (1994) J Med Chem 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

Encoded Combinatorial Libraries. In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

Encoded Combinatorial Libraries—Tagging with Sequenceable Bio-Oligomers. The principle of using oligonucleotides to encode combinatorial synthetic libraries was described in 1992 (Brenner et al. (1992) PNAS 89:5381-5383), and an example of such a library appeared the following year (Needles et al. (1993) *PNAS* 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In certain embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529-2531), orthogonality in synthesis is achieved by employing acid-labile protection for the coding strand and base-labile protection for the compound strand.

In an alternative approach (Nikolaiev et al. (1993) *Pept Res* 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

Encoded Combinatorial Libraries—Non-Sequenceable Tagging: Binary Encoding. An alternative form of encoding the test compound library employs a set of non-sequenceable electrophoric tagging molecules that are used as a binary code (Ohlmeyer et al. (1993) *PNAS* 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

General Experimental Details

Reagents. Pd(OAc)$_2$ was obtained from Englehard and used without further purification. Dichloromethane was purchased from J. T. Baker in CYCLE-TAINER® solvent delivery kegs, which were vigorously purged with argon for 2 h, and further purified by passing the solvent through two packed columns of neutral alumina and copper (II) oxide under argon pressure. All other reagents were purchased from commercial sources and used without further purification.

Analytical Methods. All reactions were carried out under an argon atmosphere. IR spectra were obtained on a Perkin-Elmer Model 2000 FT-IR using NaCl plates (thin film). $^1$H NMR and $^{13}$C NMR spectra were recorded on a Bruker 400 Mhz NMR with chemical shifts reported in ppm relative to the residual deuterated solvent or the internal standard tetramethylsilane. Yield refers to isolated yields of compounds greater than 95% purity as determined by capillary gas chromatography (GC) and proton Nuclear Magnetic Resonance spectroscopy ($^1$H NMR) analysis. $^1$H NMR and melting points (where applicable) of all known compounds were compared with those reported; literature references cited. Most compounds were further characterized by elemental analysis.

Example 2

Preparation of Water-Soluble Ligand 2 (See FIG. 1, Equation 1)

Figure 7:
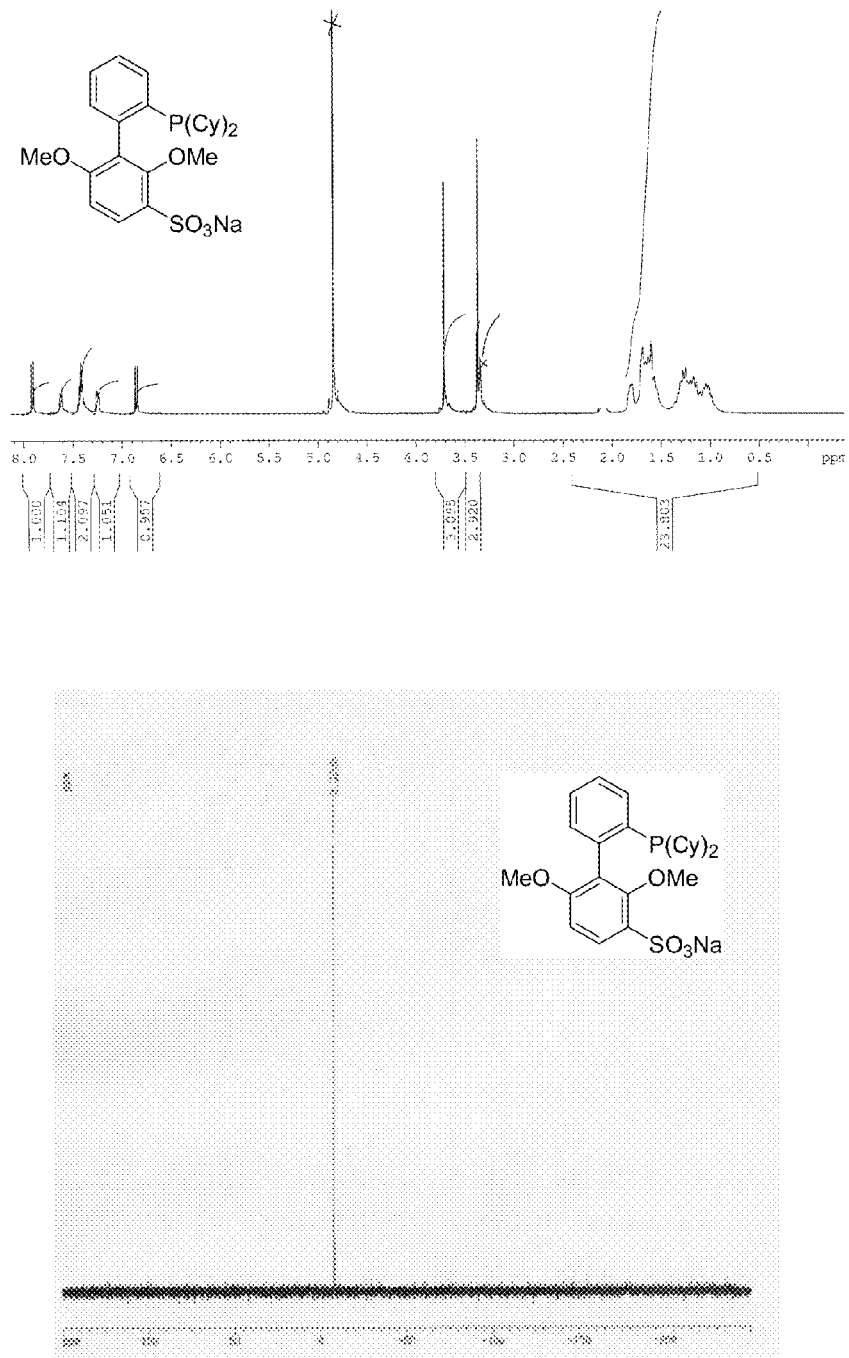
FIG. 7 depicts the $^1$H NMR spectrum (d$^4$-MeOH/D$_2$O) of ligand 2; and the $^{31}$P NMR spectrum of (d$^4$-MeOH) of ligand 2.

To an oven-dried 25 mL round bottom flask equipped with a Teflon-coated magnetic stir bar and rubber septum was added 2-dicyclohexylphosphino-2'6' dimethoxybiphenyl (5.13 g, 12.5 mmol) and CH$_2$Cl$_2$ (5 mL). The solution was cooled to 0° C. using an ice/water bath and then concentrated H$_2$SO$_4$ (32.5 mL, 625 mmol) was added dropwise. The solution slowly turned yellow in color. The solution was heated to 40° C. in a preheated oil bath and was allowed stir for 24 h. At this time it was cooled to 0° C. using an ice/water bath and crushed ice (~50 g) was added. The solution turned cloudy and white in color. An aqueous solution of NaOH (6.0 M, ~200 mL) was then added dropwise to the cooled solution until it became neutral (pH ~7.0 as judged by pH paper). The aqueous solution was extracted with CH$_2$Cl$_2$ (3×300 mL) and concentrated under reduced pressure to give a light yellow solid. The crude material was then dissolved in a minimum amount of cold methanol (~20 mL), filtered and concentrated (this cycle was repeated) to give sodium 2-dicyclohexylphosphino-2',6'-dimethoxybiphenyl-3'-sulfonate (2) as a light yellow solid (6.35 g, 99%). Mp=165° C. (turned red, dec.) $^1$H NMR (400 MHz, CD$_3$OD) δ: 7.88 (d, 1H, J=8.8 Hz), 7.60 (m, 1H), 7.36 (m, 2H), 7.22 (m, 1H), 6.76 (d, 1H, J=8.8 Hz) 3.70 (s, 3H), 3.39 (s, 3H), 1.14-2.01 (m, 22H). $^{13}$C NMR (125 MHz, CD$_3$OD) δ: 161.3, 157.1, 143.3, 142.9, 137.9, 137.8, 133.7, 133.6, 133.3, 133.2, 131.9, 130.0, 129.3, 128.0, 127.9, 127.8, 105.9, 61.6, 56.1, 50.0, 37.0, 36.9, 34.8, 34.6, 31.7, 31.6, 31.5, 31.2, 31.0, 30.8, 30.7, 28.9, 28.8, 28.7, 28.4, 28.34, 28.31, 28.2, 27.8, 27.7. $^{31}$P NMR (162 MHz, CD$_3$OD) δ: −8.02. IR (neat, cm$^{-1}$): 3453, 2925, 2849, 1577, 1462, 1448, 1400, 1229, 1191, 1099, 1053, 736. Anal. Calcd for C$_{26}$H$_{34}$NaO$_5$PS: C, 60.92; H, 6.69. Found: C, 60.40; H, 6.85. $^1$H NMR (d$^4$-MeOH/D$_2$O) is shown in FIG. 7. $^{31}$P NMR (d$^4$-MeOH) is shown in FIG. 7.

Example 3

General Procedure for Suzuki-Miyaura Coupling in Water (See FIG. 2)

A disposable tube with a screw cap, Teflon septum and stir bar was charged with Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.0200 mmol, 2 mol %), aryl halide (1.00 mmol), boronic acid (1.20-1.50 mmol) and K$_2$CO$_3$ (276-690 mg, 2.00-5.00 mmol). The tube was evacuated and back-filled with argon (this was repeated two additional times). Degassed water (1.5-3.0 mL, sonicated under vacuum for 2 min) was added and the reaction mixture was allowed to stir at the noted temperature or submitted to microwave irradiation using a CEM Discover® LabMate microwave (300 W, 150° C., with cooling to optimize the power). After cooling to room temperature, the hydrophilic products were isolated by acidifying the reaction mixture with HCl (2.0 M) to pH ~5 and extraction with ethyl acetate or diethyl ether. The organic layer was dried over anhydrous MgSO$_4$, filtered through Celite and concentrated to give the crude product. The products were purified by crystallization from water to give pure compounds (as judged by $^1$H NMR and elemental analysis). Hydrophobic products were extracted from the water layer with diethyl ether, dried over MgSO$_4$, filtered through Celite and concentrated to dryness and purified by column chromatography on silica gel (eluting with hexanes).

Example 4

Synthesis of 3,4-dimethyl-biphenyl (FIG. 2, Entry 1; F. Gavina, A. M. Costero, A. M. Gonzalez. *J. Org. Chem.* 1990, 2060.)

The general procedure described in Example 3 was used with 3,4-dimethyl-chlorobenzene (0.140 mL, 1.00 mmol), phenylboronic acid (157 mg, 1.20 mmol), Pd(OAc)$_2$ (4.5 mg, 0.020 mmol, 2 mol %), sodium 2-dicyclohexylphosphino-2',6'-dimethoxybiphenyl-3'-sulfonate (20.0 mg, 0.040 mmol, 4 mol %), K$_2$CO$_3$ (276 mg, 2.00 mmol), water (1.0 mL), 10 h, room temperature. The product was isolated as a colorless oil (151 mg, 99%). $^1$H NMR (400 MHz, CDCl$_3$) δ: 7.82 (d, 2H, J=7.6 Hz), 6.81-7.55 (m, 6H), 2.24 (s, 6H).

Example 5

Synthesis 2',6'-dimethyl-biphenyl-3-carboxylic acid amide (FIG. 2, Entry 2)

The general procedure described in Example 3 was used with 3-chlorobenzamide (0.132 mL, 1.00 mmol), 2,6-dimethylphenylboronic acid (180 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 12 h, 100° C. The product was isolated as a white solid (225 mg, 99%).

Using Microwave Irradiation. The general procedure described in Example 3 was used with 3-chlorobenzamide (156 mg, 1.00 mmol), 2,6-dimethylphenylboronic acid (180 mg, 1.20 mmol), Pd(OAc)$_2$ (4.5 mg, 0.020 mmol, 2 mol %), sodium 2-dicyclohexylphosphino-2',6'-dimethoxybiphenyl-3'-sulfonate (20.0 mg, 0.0391 mmol, 4 mol %), K$_2$CO$_3$ (345 mg, 2.50 mmol), water (3.0 mL), 10 min, 150° C. (microwave irradiation with cooling). The product was isolated as a white solid (207 mg, 92%). Mp=123-125° C. $^1$H NMR (400 MHz, CDCl$_3$) δ: 7.85 (d, 1H, J=7.6 Hz), 7.67 (s, 1H), 7.50 (t, 1H, J=7.6 Hz), 7.33 (d, 1H, J=7.6 Hz), 7.20 (t, 1H, J=7.4 Hz), 7.13 (d, 2H, J=7.2 Hz), 6.87 (br-s, 1H), 6.69 (br-s, 1H), 2.03 (s, 6H). $^{13}$C NMR (125 MHz, CDCl$_3$) δ: 170.1, 141.6, 140.8, 135.9, 133.8, 132.8, 128.9, 128.1, 127.5, 126.0, 20.96. IR (neat, cm$^{-1}$): 3347 (br), 3197 (br), 1657, 1602, 1578, 1379, 1102, 770, 737, 703. Anal. Calcd for C$_{15}$H$_{15}$NO: C, 79.97; H, 6.71. Found: C, 79.98; H, 6.48.

Example 6

Synthesis of biphenyl-3-carboxylic acid (FIG. 2, Entry 3; N. E. Leadbeater, S. M. Resouly, *Tetrahedron* 1999, 55, 11889.)

Using 2 Mol % Pd. The general procedure described in Example 3 was used with 3-chlorobenzoic acid (157 mg, 1.00 mmol), phenylboronic acid (145 mg, 1.20 mmol), Pd(OAc)$_2$ (4.5 mg, 0.020 mmol, 2 mol %), sodium 2-dicyclohexylphosphino-2',6'-dimethoxybiphenyl-3'-sulfonate (20.0 mg, 0.040 mmol, 4 mol %), K$_2$CO$_3$ (345 mg, 2.50 mmol), water (1.5 mL), 2 h, room temperature. The product was isolated as a white solid (190 mg, 96%).

Using 0.5 Mol % Pd. The general procedure described in Example 3 was used with 3-chlorobenzoic acid (157 mg, 1.00 mmol), phenylboronic acid (145 mg, 1.20 mmol), Pd(OAc)$_2$ (1.1 mg, 0.005 mmol, 0.5 mol %), sodium 2-dicyclohexylphosphino-2',6'-dimethoxybiphenyl-3'-sulfonate (5.0 mg, 0.010 mmol, 1 mol %), K$_2$CO$_3$ (345 mg, 2.50 mmol), water (1.5 mL), 8 h, room temperature. The product was isolated as a white solid (192 mg, 97%).

Using 0.1 Mol % Pd. The general procedure described in Example 3 was used with 3-chlorobenzoic acid (157 mg, 1.00 mmol), phenylboronic acid (145 mg, 1.20 mmol), K$_2$CO$_3$ (345 mg, 2.50 mmol), water (1.5 mL), Pd/L solution (0.200 mL of a Pd(OAc)$_2$ (1.1 mg, 0.005 mmol, 0.5 mol %), sodium 2-dicyclohexylphosphino-2',6'-dimethoxybiphenyl-3'-sulfonate (5.0 mg, 0.010 mmol, 1 mol) in 1.0 mL water), 5 h, 100° C. The product was isolated as a white solid (192 mg, 97%).

Using 0.1 Mol % Pd and Microwave Irradiation. The general procedure described in Example 3 was used with 3-chlorobenzoic acid (157 mg, 1.00 mmol), phenylboronic acid (145 mg, 1.20 mmol), K$_2$CO$_3$ (345 mg, 2.50 mmol), water (1.5 mL), Pd/L solution (0.200 mL of a Pd(OAc)$_2$ (1.1 mg, 0.005 mmol, 0.5 mol %), sodium 2-dicyclohexylphosphino-2',6'-dimethoxybiphenyl-3'-sulfonate (5.0 mg, 0.010 mmol, 1 mol %) solution in 1.0 mL water), 10 min, 150° C. (microwave irradiation with cooling). The product was isolated as a white solid (192 mg, 97%). Mp=164° C. (lit.=165-166° C.) $^1$H NMR (400 MHz, CDCl$_3$) δ: 11.90 (br-s, 1H), 8.41 (s, 1H), 8.15 (d, 1H, J=7.6 Hz), 7.88 (d, 1H, J=7.6 Hz), 7.68 (d, 2H, J=7.2 Hz), 7.60 (t, 1H, J=6.4 Hz), 7.52 (t, 2H, J=7.6 Hz), 7.43 (t, 1H, J=7.2 Hz). $^{13}$C NMR (125 MHz, CDCl$_3$) δ: 172.6, 141.8, 140.1, 132.7, 130.0, 129.3, 129.2, 129.1, 129.0, 128.0, 127.4.

Example 7

Synthesis of 2'-methyl-biphenyl-3-carboxylic acid (FIG. 2, Entry 4)

Using 0.5 Mol % Pd. The general procedure described in Example 3 was used with 3-chlorobenzoic acid (157 mg, 1.00 mmol), o-tolylboronic acid (163 mg, 1.20 mmol), Pd(OAc)$_2$ (1.1 mg, 0.005 mmol, 0.5 mol %), sodium 2-dicyclohexylphosphino-2',6'-dimethoxybiphenyl-3'-sulfonate (5.0 mg, 0.010 mmol, 1 mol %), K$_2$CO$_3$ (345 mg, 2.50 mmol), water (1.5 mL), 8 h, room temperature. The product was isolated as a white solid (201 mg, 95%).

Using 0.1 Mol % Pd. The general procedure described in Example 3 was used with 3-chlorobenzoic acid (157 mg, 1.00 mmol), o-tolylboronic acid (163 mg, 1.20 mmol), K$_2$CO$_3$ (345 mg, 2.50 mmol), water (1.5 mL), Pd/L solution (0.200 mL of a Pd(OAc)$_2$ (1.1 mg, 0.005 mmol, 0.5 mol %), sodium 2-dicyclohexylphosphino-2',6'-dimethoxybiphenyl-3'-sulfonate (5.0 mg, 0.010 mmol, 1 mol %) solution in 1.0 mL water), 6 h, 100° C. The product was isolated as a white solid (203 mg, 96%). Mp=127° C. $^1$H NMR (400 MHz, CDCl$_3$) δ: 12.9 (br-s, 1H), 8.01 (m, 2H), 7.46 (d, 1H, J=7.6 Hz), 7.40 (t, 1H, J=7.6 Hz), 7.20-7.14 (m, 4H), 2.17 (s, 3H). $^{13}$C NMR (125 MHz, CDCl$_3$) δ: 172.8, 142.5, 140.8, 135.5, 134.8, 131.1, 130.7, 129.9, 129.4, 128.8, 128.5, 127.9, 125.2, 20.6. IR (neat, cm$^{-1}$): 2962, 1689, 1309, 1258, 747. Anal. Calcd for C$_{14}$H$_{12}$O$_2$: C, 79.22; H, 5.70. Found: C, 79.12; H, 5.62.

Example 8

Synthesis of 4-hydroxy-2'-methyl-biphenyl-3-carboxylic acid (FIG. 2, Entry 5)

Using 2 Mol % Pd. The general procedure described in Example 3 was used with 5-chloro-2-hydroxy-benzoic acid (173 mg, 1.00 mmol), 2-methylphenylboronic acid (163 mg, 1.20 mmol), Pd(OAc)$_2$ (4.5 mg, 0.020 mmol, 2 mol %), sodium 2-dicyclohexylphosphino-2',6'-dimethoxybiphenyl-3'-sulfonate (20.0 mg, 0.040 mmol, 4 mol %), K$_2$CO$_3$ (483 mg, 3.50 mmol), water (2.0 mL), 12 h, room temperature. The product was isolated as a white solid (227 mg, 99%).

Using 0.1 Mol % Pd. The general procedure described in Example 3 was used with 5-chloro-2-hydroxy-benzoic acid (173 mg, 1.00 mmol), 2-methylphenylboronic acid (163 mg, 1.20 mmol), K$_2$CO$_3$ (345 mg, 2.50 mmol), water (2.0 mL), Pd/L solution (0.200 mL of a Pd(OAc)$_2$ (1.1 mg, 0.005 mmol, 0.5 mol %), sodium 2-dicyclohexylphosphino-2',6'-dimethoxybiphenyl-3'-sulfonate (5.0 mg, 0.010 mmol, 1 mol %) solution in 1.0 mL water), 12 h, 100° C. The product was isolated as a white solid (217 mg, 96%). Mp=151° C. (lit. 150-152° C.). $^1$H NMR (400 MHz, CDCl$_3$) δ: 11.91 (br-s, 1H), 10.28 (br-s, 1H), 7.83 (d, 1H, J=2.0 Hz), 7.42 (dd, 1H, J=2.4 Hz, J=8.6 Hz), 7.20-7.13 (m, 4H), 6.98 (d, 1H, J=8.4 Hz), 2.20 (s, 3H). $^{13}$C NMR (125 MHz, CDCl$_3$) δ: 175.4, 161.3, 140.4, 138.2, 135.6, 133.7, 131.4, 130.7, 129.9, 127.4, 126.2, 117.9, 111.2, 20.7 IR (neat, cm$^{-1}$): 3062, 1664, 1614, 1583, 1478, 1440, 1229, 1190, 728.

Example 9

Synthesis of 2,4,6,2'-tetramethyl-biphenyl (FIG. 2, Entry 6; A. Littke, C. Dai, G. C. Fu *J. Am. Chem. Soc.* 2000, 122, 4020.)

The general procedure described in Example 3 was used with 2-bromo-mesitylene (0.153 mL, 1.00 mmol), 2-methylphenylboronic acid (203 mg, 1.50 mmol), Pd(OAc)$_2$ (4.5 mg, 0.020 mmol, 2 mol %), sodium 2-dicyclohexylphosphino-2',6'-dimethoxybiphenyl-3'-sulfonate (20.0 mg, 0.040 mmol, 4 mol %), K$_2$CO$_3$ (276 mg, 2.00 mmol), water (1.5 mL), 22 h, room temperature. The product was isolated as a colorless oil (197 mg, 94%). $^1$H NMR (400 MHz, CDCl$_3$) δ:

7.30-7.19 (m, 3H), 7.05-7.00 (m, 1H), 6.92 (s, 2H), 2.30 (2, 3H), 1.99 (s, 3H), 1.89 (s, 6H). $^{13}$C NMR (125 MHz, CDCl$_3$) δ: 140.9, 138.2, 136.4, 136.0, 135.9, 130.0, 129.2, 128.1, 127.1, 126.2, 21.4, 20.6, 19.9.

Example 10

Synthesis of 2,6,2'-trimethyl-biphenyl (FIG. 2, Entry 7; A. Littke, C. Dai, G. C. Fu *J. Am. Chem. Soc.* 2000, 122, 4020.)

The general procedure described in Example 3 was used with 2-bromotoluene (0.120 mL, 1.00 mmol), 2,6-dimethylphenylboronic acid (225 mg, 1.50 mmol), Pd(OAc)$_2$ (4.5 mg, 0.020 mmol, 2 mol %), sodium 2-dicyclohexylphosphino-2',6'-dimethoxybiphenyl-3'-sulfonate (20.0 mg, 0.040 mmol, 4 mol %), K$_2$CO$_3$ (276 mg, 2.00 mmol), water (1.5 mL), 22 h, room temperature. The product was isolated as a colorless oil (190 mg, 97%). $^1$H NMR (400 MHz, CDCl$_3$) δ: 7.30-7.10 (m, 6H), 7.02-7.00 (m, 1H), 1.99 (s, 3H), 1.96 (s, 6H). $^{13}$C NMR (125 MHz, CDCl$_3$) δ: 141.1, 140.7, 136.1, 135.9, 130.0, 129.1, 127.4, 127.1, 127.1, 126.1, 20.7, 19.7.

Example 11

Synthesis of biphenyl-3,4'-dicarboxylic acid (FIG. 3, Entry 1; K. M. Lawson Daku, R. F. Newton, S. P. Pearce, J. Vile, J. M. J. Williams, *Tetrahedron Lett.* 2003, 44, 5095; and J. B. Bapat, R. F. C. Brown, G. H. Bulmer, T. Childs, K. J. Coulston, F. W. Eastwood, D. K. Taylor *Australian J. Chem.* 1997, 50, 1159.)

The general procedure described in Example 3 was used with 4-chlorobenzoic acid (157 mg, 1.00 mmol), 3-carboxyphenylboronic acid (199 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (3.0 mL), 8 h, 50° C. The product was isolated as a white solid (241 mg, 99%).

Using Microwave Irradiation. The general procedure described in Example 3 was used with 4-chlorobenzoic acid (157 mg, 1.00 mmol), 3-carboxyphenylboronic acid (199 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (3.0 mL), 10 min at 150° C. (using microwave irradiation with cooling). The product was isolated as a white solid (229 mg, 95%). Mp=>250° C. (lit. mp=295° C.). $^1$H NMR (400 MHz, d$^6$-DMSO/D$_2$O) δ: 8.22 (s, 1H), 8.42 (d, 2H, J=7.6 Hz), 7.98 (d, 1H, J=7.6 Hz), 7.91 (d, 1H, J=7.6 Hz), 7.79 (d, 2H, J=7.6 Hz), 7.59 (t, 1H, J=7.2 Hz). $^{13}$C NMR (125 MHz, d$^6$-DMSO/D$_2$O) δ: 167.5, 143.6, 139.7, 131.9, 131.7, 130.4, 130.3, 129.8, 129.4, 127.8, 127.2.

Example 12

Synthesis of 2'-hydroxy-biphenyl-4-carboxylic acid (FIG. 3, Entry 2)

The general procedure described in Example 3 was used with 4-chlorobenzoic acid (157 mg, 1.00 mmol), 2-hydroxyphenylboronic acid (166 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 12 h, 100° C. The product was isolated as a white solid (203 mg, 95%). Mp=186° C. $^1$H NMR (400 MHz, d$^4$-MeOH) δ: 8.04 (d, 2H, J=8.4 Hz), 7.65 (d, 2H, J=8.4 Hz), 7.25 (dd, 1H, J=7.6 Hz, 1.6 Hz), 7.16 (td, 1H, J=7.6 Hz, 1.6 Hz), 6.89 (m, 2H). $^{13}$C NMR (125 MHz, d$^4$-MeOH) δ: 170.2, 155.6, 145.4, 131.7, 130.5 (2), 130.48, 130.4, 129.8, 128.7, 121.2, 117.2. IR (neat, cm$^{-1}$): 3391, 2529, 1683, 1274, 1008, 753.

Example 13

Synthesis of 2'-amino-biphenyl-3-carboxylic acid (FIG. 3, Entry 3; C. L. Nesloney, J. W. Kelly *J. Org. Chem.* 1996, 61, 3127.)

The general procedure described in Example 3 was used with 3-chlorobenzoic acid (157 mg, 1.00 mmol), 2-aminophenylboronic acid (205 mg, 1.50 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 12 h, 100° C. The product was isolated as a white solid (203 mg, 95%). Mp=170° C. (lit.=173-175° C.) $^1$H NMR (400 MHz, d$^4$-MeOH) δ: 8.07 (m, 1H), 7.99 (d, 1H, J=7.6 Hz), 7.65 (d, 1H, J=8.0 Hz), 7.53 (t, 1H, J=7.6 Hz), 7.13 (td, 1H, J=1.6 Hz, J=7.6 Hz), 6.84 (d, 1H, J=8.0 Hz), 6.77 (t, 1H, J=7.6 Hz). $^{13}$C NMR (125 MHz, d$^4$-MeOH) δ: 169.9, 145.1, 141.7, 134.8, 132.6, 131.4, 131.4, 130.1, 129.9, 129.5, 128.3, 120.0, 117.6.

Example 14

Synthesis of 2'-acetyl-biphenyl-3-carboxylic acid (FIG. 3, Entry 3)

The general procedure described in Example 3 was used with 3-chlorobenzoic acid (157 mg, 1.00 mmol), 2-acetylphenylboronic acid (179 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 10 h, 100° C. The product was isolated as a light yellow solid (233 mg, 97%). Mp=143° C. $^1$H NMR (400 MHz, CDCl$_3$) δ: 12.60 (br-s, 1H), 8.05 (m, 1H), 7.65 (d, 1H, J=7.2 Hz), 7.58-7.55 (m, 3H), 7.49 (d, 1H, J=7.2 Hz), 7.42 (d, 1H, J=7.6 Hz), 2.16 (s, 3H). $^{13}$C NMR (125 MHz, CDCl$_3$) δ: 204.3, 172.2, 141.7, 140.7, 139.9, 134.7, 131.5, 131.0, 130.7, 130.3, 129.9, 129.2, 128.7, 128.4, 30.8. IR (neat, cm$^{-1}$): 3419, 2517, 1686, 1018. Anal. Calcd for C$_{15}$H$_{12}$O$_3$: C, 74.99; H, 5.03. Found: C, 75.04; H, 5.06.

Example 15

Synthesis of 2'-formyl-biphenyl-3-carboxylic acid monohydrate (FIG. 3, Entry 3; C. G. Blettner, W. A. Konig, G. Ruhter, W. Stenzel, T. Schotten *Synlett* 1999 307; and C. G. Blettner, W. A. Konig, W. Stenzel, T. Schotten *Synlett* 1998 295.)

The general procedure described in Example 3 was used with 3-chlorobenzoic acid (157 mg, 1.00 mmol), 2-formylphenylboronic acid (225 mg, 1.50 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 10 h, 80° C. The product was isolated as a white solid (192 mg, 85%). Mp=164-167° C. $^1$H NMR (400 MHz, d$^4$-MeOH, d$^6$-DMSO) δ: 8.07 (m, 2H), 7.68 (m, 1H), 7.63-7.52 (m, 2H), 7.46 (m, 2H), 7.30 (m, 1H), 5.10 (s, 1H), 4.98

(br-s, 2H). $^{13}$C NMR (125 MHz, d$^4$-MeOH, d$^6$-DMSO) δ: 169.4, 142.1. 142.0, 137.0, 135.0, 131.9, 131.7, 131.2, 129.9, 129.8, 129.6, 128.9, 127.8, 103.6 [Ar—CH(OH)$_2$] IR (neat, cm$^{-1}$): 3066, 1694, 1260, 754.

Example 16

Synthesis of 4'-cyano-4-hydroxy-biphenyl-3-carboxylic acid (FIG. 3, Entry 4)

The general procedure described in Example 3 was used with 5-chloro-2-hydroxy-benzoic acid (173 mg, 1.00 mmol), 4-cyanophenylboronic acid (176 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (552 mg, 4.00 mmol), water (2.0 mL), 12 h, 80° C. The product was isolated as a white solid (220 mg, 92%). Mp=227° C. $^1$H NMR (400 MHz, d$^4$-MeOH) δ: 8.11 (d, 1H, J=2.4 Hz), 7.81-7.70 (m, 5H), 7.02 (d, 1H, J=8.4 Hz). $^{13}$C NMR (125 MHz, d$^4$-MeOH) δ: 173.2, 163.5, 145.5, 135.4, 134.0, 131.2, 130.1, 128.3, 120.1, 119.4, 114.6, 111.5. IR (neat, cm$^{-1}$): 3429, 2229, 1667, 750. Anal. Calcd for C$_{14}$H$_9$NO$_3$: C, 70.29; H, 3.79. Found: C, 69.96; H, 3.52.

Example 17

Synthesis of 2,3'-diamino-biphenyl-4-carboxylic acid (FIG. 3, Entry 5)

The general procedure described in Example 3 was used with 3-amino-4-chloro-benzoic acid (172 mg, 1.00 mmol), 3-aminophenylboronic acid (190 mg, 1.40 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (552 mg, 4.00 mmol), water (3.0 mL), 12 h, 100° C. The product was isolated as a light brown oil (254 mg, 99%). $^1$H NMR (400 MHz, CDCl$_3$/d$^4$-MeOH) δ: 7.35 (m, 2H), 7.10 (t, 1H, J=7.6 Hz), 7.02 (d, 1H, J=8.0 Hz), 6.70-6.60 (m, 3H). $^{13}$C NMR (125 MHz, CDCl$_3$/d$^4$-MeOH) δ: 169.4, 146.6, 143.4, 139.4, 132.4, 129.9, 129.7, 129.0, 119.8, 118.9, 115.8, 115.5, 114.8. IR (neat, cm$^{-1}$): 3419, 1645, 1016. ELMS for C$_{13}$H$_{12}$N$_2$O$_2$: Theoretical [M+H]= 229.0977. Found: 229.0982. Anal. Calcd for C$_{13}$H$_{12}$N$_2$O$_2$: C, 68.41; H, 5.30. Found: C, 68.29; H, 5.29.

Example 18

Synthesis of toluene-4-sulfonic acid monohydrate (FIG. 3, Entry 6; J. H. Jones, M. E. Wood *Syn. Comm.* 1986, 16, 1515.)

The general procedure described in Example 3 was used with 4-chlorobenzenesulfonic acid (192 mg, 1.00 mmol), methylboronic acid (90 mg, 1.50 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 12 h, 100° C. The product was isolated as a white solid (207 mg, 99%). Mp=104° C. (lit.=106° C.). $^1$H NMR (400 MHz, d$^4$-MeOH) δ: 7.71 (d, 2H, J=8.4 Hz), 7.24 (d, 2H, J=8.4 Hz), 5.08 (s, H$_2$O), 2.37 (s, 3H)). $^{13}$C NMR (125 MHz, d$^4$-MeOH) δ: 143.3, 142.0, 130.0, 127.1, 21.4.

Example 19

Synthesis of 2',4'-difluoro-biphenyl-4-sulfonic acid amide (FIG. 3, Entry 7)

The general procedure described in Example 3 was used with 4-chloro-benzenesulfonamide (192 mg, 1.00 mmol), 2,4-difluorophenylboronic acid (205 mg, 1.30 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 12 h, 80° C. The product was isolated as a white solid (258 mg, 96%). Mp=143° C. $^1$H NMR (400 MHz, d$^4$-MeOH) δ: 7.98 (d, 2H, J=8.4 Hz), 7.87 (d, 1H, J=8.4 Hz), 7.63 (d, 2H, J=7.2 Hz), 7.49 (d, 2H, J=8.4 Hz), 7.05-6.99 (m, 2H). $^{13}$C NMR (125 MHz, d$^4$-MeOH) δ: 165.5 (d), 163.0 (d), 162.3 (d), 159.8 (d), 144.0, 143.6, 140.0, 139.3, 133.1 (d), 133.0 (d), 130.5 (d), 130.2, 128.9, 127.4, 125.1 (d), 124.9 (d), 113.2 (d), 113.0 (d), 105.4 (t). IR (neat, cm$^{-1}$): 3362, 3257, 1619, 1599, 1516, 1487, 1302, 1103, 965, 849, 809. Anal. Calcd for C$_{12}$H$_9$F$_2$NO$_2$S: C, 53.53; H, 3.37. Found: C, 53.34; H, 3.36.

Example 20

Synthesis of 3,5-dimethyl-4-phenoxathiin-4-yl-phenol (FIG. 4, Entry 1)

The general procedure described in Example 3 was used with 4-chloro-3,5-dimethyl-phenol (156 mg, 1.00 mmol), 4-phenoxathiineboronic acid (293 mg, 1.20 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (3.0 mL), 12 h, 100° C. The product was isolated as a colorless oil (277 mg, 85%), which became a white solid upon standing. Mp=116° C. $^1$H NMR (400 MHz, CDCl$_3$) δ: 7.20 (m, 2H), 7.01-7.16 (m, 3H), 6.96 (d, 1H, J=7.6 Hz), 6.73 (m, 3H), 5.64 (s, 1H), 2.04 (s, 6H). $^{13}$C NMR (125 MHz, CDCl$_3$) δ: 154.6, 152.6, 149.9, 138.3, 130.2, 129.9, 129.5, 127.8, 126.8, 126.1, 124.7, 124.6, 121.2, 121.1, 118.2, 114.2, 20.9. IR (neat, cm$^{-1}$): 3367, 1593, 1471, 1419, 1311, 1265, 1223, 1154, 1026, 752. Anal. Calcd for C$_{20}$H$_{16}$O$_2$S: C, 74.97; H, 5.03. Found: C, 74.88; H, 4.99.

Example 21

Synthesis of 5-(4-methoxy-phenyl)-1H-indole-2-carboxylic acid (FIG. 4, Entry 2)

The general procedure described in Example 3 was used with 5-chloro-1H-indole-2-carboxylic acid (194 mg, 1.00 mmol), 4-methoxyphenylboronic acid (207 mg, 1.50 mmol), Pd(OAc)$_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), K$_2$CO$_3$ (414 mg, 3.00 mmol), water (2.0 mL), 12 h, 80° C. The product was isolated as a light yellow solid (246 mg, 93%). Mp=>230° C. $^1$H NMR (400 MHz, d$^6$-DMSO) δ: 11.81 (s, 1H), 7.84 (s, 1H), 7.58 (d, 2H, J=8.8 Hz), 7.49 (m, 2H), 7.13 (d, 1H, J=1.6 Hz), 6.99 (d, 2H, J=8.4 Hz), 3.78 (s, 3H). $^{13}$C NMR (125 MHz, d$^6$-DMSO) δ: 162.7, 158.3, 136.3, 133.7, 132.2, 129.0, 127.7, 127.5, 123.7, 119.1, 114.3, 112.8, 107.7, 55.1. IR (neat, cm$^{-1}$): 4320, 1700, 1183. Anal. Calcd for C$_{16}$H$_{13}$NO$_3$: C, 71.90; H, 4.90. Found: C, 71.94; H, 4.93.

Example 22

Synthesis of 2-(3'-acetyl-biphenyl-4-yloxy)-nicotinic acid (FIG. 4, Entry 3)

The general procedure described in Example 3 was used with 2-(4-chloro-phenoxy)-nicotinic acid (250 mg, 1.00 mmol), 3-acetylphenylboronic acid (246 mg, 1.50 mmol), $Pd(OAc)_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), $K_2CO_3$ (414 mg, 3.00 mmol), water (2.0 mL), 12 h, 80° C. The product was isolated as a white solid (305 mg, 92%). Mp=188° C. $^1H$ NMR (400 MHz, $d^6$-DMSO) δ: 8.27 (m, 2H), 8.20 (s, 1H), 7.93 (d, 2H, J=7.6 Hz), 7.77 (d, 2H, J=8.8 Hz), 7.61 (t, 1H, J=7.6 Hz), 7.23 (m, 3H), 2.66 (s, 3H). $^{13}C$ NMR (125 MHz, $d^6$-DMSO) δ: 198.0, 166.0, 160.7, 153.9, 150.3, 141.5, 140.0, 137.5, 135.6, 131.3, 129.4, 128.2, 126.9, 126.4, 121.9, 119.1, 117.2, 26.9. IR (neat, $cm^{-1}$): 3000-4000 (br), 1674, 1651, 1585, 1418, 1231, 896, 770. Anal. Calcd for $C_{20}H_{15}NO_4$: C, 72.06; H, 4.54. Found: C, 71.68; H, 4.41.

Example 23

Synthesis of [2,3']bipyridinyl-6-ylamine (FIG. 4, Entry 4)

The general procedure described in Example 3 was used with 6-chloro-pyridin-2-ylamine (129 mg, 1.00 mmol), 3-pyridylboronic acid (184 mg, 1.50 mmol), $Pd(OAc)_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), $K_2CO_3$ (414 mg, 3.00 mmol), water (2.0 mL), 12 h, 100° C. The product was purified by column chromatography on silica gel (eluting with ethyl acetate/methanol, 9.5/0.5) to give the desired product as a white solid (145 mg, 85%). Mp=108° C. $^1H$ NMR (400 MHz, $d^4$-MeOH) δ: 8.69 (d, 1H, J=4.8 Hz), 8.43 (dd, 1H, J=4.8 Hz, 1.6 Hz), 8.19 (d, 1H, J=4.8 Hz), 7.96 (dq, 1H, J=8.0 Hz, 1.6 Hz, 0.4 Hz), 7.75 (dd, 1H, J=8.8 Hz, 2.4 Hz), 7.44 (qd, 1H, J=4.8 Hz, 8.8 Hz), 6.68 (d, 1H, J=8.4 Hz). $^{13}C$ NMR (125 MHz, $d^4$-MeOH) δ: 161.0, 148.2, 147.4, 146.5, 137.9, 136.0, 135.4, 125.6, 123.4, 110.6. IR (neat, $cm^{-1}$): 3396 (br), 2522, 1633, 1018. EI-MS: Theoretical [M+H]=172.0869. Found: 172.0868. Anal. Calcd for $C_{10}H_9N_3$: C, 70.16; H, 5.30. Found: C, 69.89; H, 5.25.

Example 24

Synthesis of 5-furan-3-yl-thiophene-2-carboxylic acid (FIG. 4, Entry 5)

The general procedure described in Example 3 was used with 5-bromothiophene carboxylic acid (206 mg, 1.00 mmol), 3-furanboronic acid (168 mg, 1.50 mmol), $Pd(OAc)_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), $K_2CO_3$ (414 mg, 3.00 mmol), water (5.0 mL), 12 h, 100° C. The product was isolated as a white solid (181 mg, 94%).

Using Microwave Irradiation. The general procedure was used with 5-bromothiophene carboxylic acid (206 mg, 1.00 mmol), 3-furanboronic acid (168 mg, 1.50 mmol), $Pd(OAc)_2$ (2.2 mg, 0.010 mmol, 1 mol %), sodium 2-dicyclohexylphosphino-2',6'-dimethoxybiphenyl-3'-sulfonate (10.0 mg, 0.020 mmol, 2 mol %), $K_2CO_3$ (414 mg, 3.00 mmol), water (5.0 mL), 10 min, 150° C. (using microwave irradiation with cooling). The product was isolated as a white solid (183 mg, 95%). Mp=147° C. $^1H$ NMR (400 MHz, $d^4$-MeOH) δ: 7.89 (m, 1H), 7.65 (d, 1H, J=4.0 Hz), 7.54 (t, 1H, J=1.6 Hz), 7.15 (d, 1H, J=4.0 Hz), 6.69 (m, 1H). $^{13}C$ NMR (125 MHz, $d^4$-MeOH) δ: 165.4, 145.6, 143.7, 140.9, 135.5, 132.9, 125.2, 121.5, 109.9. IR (neat, $cm^{-1}$): 3200 (br), 1672, 1287. Anal. Calcd for $C_9H_6O_3S$: C, 55.66; H, 3.11. Found: C, 55.50; H, 3.32.

Example 25

Synthesis of biphenyl-3-carboxylic acid (N. E. Leadbeater, S. M. Resouly, *Tetrahedron* 1999, 55, 11889.)

The general procedure described in Example 3 was used with 3-chlorobenzoic acid (157 mg, 1.00 mmol), phenylboronic acid (145 mg, 1.20 mmol), $Pd(OAc)_2$ (4.5 mg, 0.020 mmol, 2 mol %), sodium 2-dicyclohexylphosphino-2',6'-dimethoxybiphenyl-3'-sulfonate (20.0 mg, 0.040 mmol, 4 mol %), $K_2CO_3$ (345 mg, 2.50 mmol), solvent (see FIG. 5) (2.0 mL), 14 h, temperature. The conversion and yield were determined using $^1H$ NMR.

Example 26

Preparation of Water-Soluble Ligand 4 (FIG. 1, Equation 3)

To an oven-dried 25 mL round bottom flask equipped with a Teflon-coated magnetic stir bar and rubber septum was added dicyclohexyl-(2',4',6'-triisopropyl-biphenyl-2-yl)-phosphane (476 mg, 1.00 mmol) and $CH_2Cl_2$ (1.0 mL). The solution was cooled to 0° C. using an ice/water bath and then concentrated $H_2SO_4$ (1.00 mL) and fuming sulfuric acid (3.0 mL, 20% $SO_3$) were added dropwise. The solution was allowed to warm to room temperature and stir for 24 h. At this time it was cooled to 0° C. using an ice/water bath and crushed ice (~10 g) was added. The solution turned cloudy and white in color. An aqueous solution of NaOH (6.0 M, ~20.0 mL) was then added dropwise to the cooled solution until it became neutral (pH ~7.0 as judged by pH paper). The aqueous solution was extracted with $CH_2Cl_2$ (3×50 mL) and concentrated under reduced pressure to give a beige solid. The crude material was then dissolved in a minimum amount of cold methanol (~20 mL), filtered and concentrated (this cycle was repeated) to give sodium 2'-(dicyclohexyl-phosphanyl)-2,6-diisopropyl-biphenyl-4-sulfonate (4) as a beige solid (503 mg, 94%). Mp=>250° C. $^1H$ NMR (400 MHz, $CD_3OD$) δ: 7.52 (s, 2H), 7.46 (m, 1H), 7.22 (m, 2H), 6.90 (m, 1H), 2.24 (m, 1H), 0.71-1.83 (34H). $^{13}C$ NMR (125 MHz, $CD_3OD$) δ: 148.4, 147.9, 147.8, 147.5, 145.6, 142.8, 137.4, 137.2, 133.92, 133.91, 132.43, 132.42, 129.3, 128.1, 121.3, 121.0, 40.1, 39.9, 39.7, 39.5, 39.3, 38.8, 35.8, 35.7, 32.5, 32.3, 31.9, 30.8, 30.6, 28.7, 28.6, 28.4, 28.3, 27.7, 26.0, 25.9, 23.3, 23.1. $^{31}P$ NMR (162 MHz, $CD_3OD$) δ: −10.7. IR (neat, $cm^{-1}$): 3459, 2927, 2851, 1634, 1463, 1447, 1184, 1078, 1040. Anal. Calcd for $C_{30}H_{42}NaO_3PS$: C, 67.14; H, 7.89. Found: C, 66.93; H, 7.77.

Example 27

General Procedure for Sonogashira Coupling in Water/Acetonitrile (FIG. 6)

A disposable tube with a screw cap, Teflon septum and stir bar was charged with $PdCl_2(CH_3CN)_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), aryl halide (0.500 mmol) and Cs$_2$CO$_3$ (406-813 mg, 1.25-2.50 mmol). The tube was evacuated and back-filled with argon (this was repeated two additional times). Acetonitrile (3.0 mL) was added and the reaction mixture was allowed to stir at room temperature for 20 minutes. The alkyne (0.650 mmol) and degassed water (1.0-1.5 mL, sonicated under vacuum for 2 min) were added and the reaction mixture was allowed to stir at the noted temperature. After cooling to room temperature the following work-up procedure was followed:

For FIG. 6, Entries 1, 2, 4 and 8. The reaction mixture was acidified with HCl (2.0 M) to pH ~5 (as judged by pH paper) and extracted out with ethyl acetate. The organic layer was dried over anhydrous MgSO$_4$, filtered through Celite and concentrated to give the crude product. To the crude material was added diethyl ether (10.0 mL), methanol (5.0 mL) and then trimethylsilyldiazomethane (2.0 mL, 2.0 M solution in dietyl ether, 4.0 mmol). The solution was allowed to stir for 5 minutes after which it was filtered and concentrated. The product was purified by column chromatography on silica gel (eluting with ether/hexane mixtures).

For FIG. 6, Entries 6 and 7. The products were extracted out of the water layer with ethyl acetate, dried over MgSO$_4$, filtered through Celite and concentrated to dryness. The product was purified by column chromatography on silica gel (eluting with hexanes).

For FIG. 6, Entries 3 and 5. The reaction was acidified with HCl (2.0 M) to pH ~5 (as judged by pH paper) and extracted out with ethyl acetate. The organic layer was dried over anhydrous MgSO$_4$, filtered through Celite and concentrated to give the crude product. The product was purified by crystallization from water.

Example 28

Synthesis of (3-methoxy-phenyl)-propynoic acid methyl ester (FIG. 6, Entry 1; S.-T. Lin, L.-C. Chen *J. Chem. Res. Synop.* 2004, 5, 353.)

The general procedure described in Example 27 was used with 3-bromoanisole (0.063 mL, 0.50 mmol), propiolic acid (added at 0° C.) (0.050 mL, 0.65 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.0 mL), 12 h, 60° C. The product was isolated as a colorless oil (66 mg, 69%). $^1$H NMR (400 MHz, CDCl$_3$) δ: 7.28 (t, 1H, J=7.6 Hz, 8.4 Hz), 7.17 (dt, 1H, J=1.2 Hz, 7.6 Hz), 7.09 (m, 1H), 7.00 (qd, 1H, J=1.2 Hz, 2.4 Hz, 8.4 Hz), 3.84 (s, 3H), 3.80 (s, 3H). $^{13}$C NMR (125 MHz, CDCl$_3$) δ: 159.4, 154.6, 129.9, 125.6, 120.5, 117.7, 117.6, 86.6, 80.2, 55.5, 52.9.

Example 29

Synthesis of 3-methoxycarbonylethynyl-benzoic acid methyl ester (FIG. 6, Entry 2)

Figure 8:
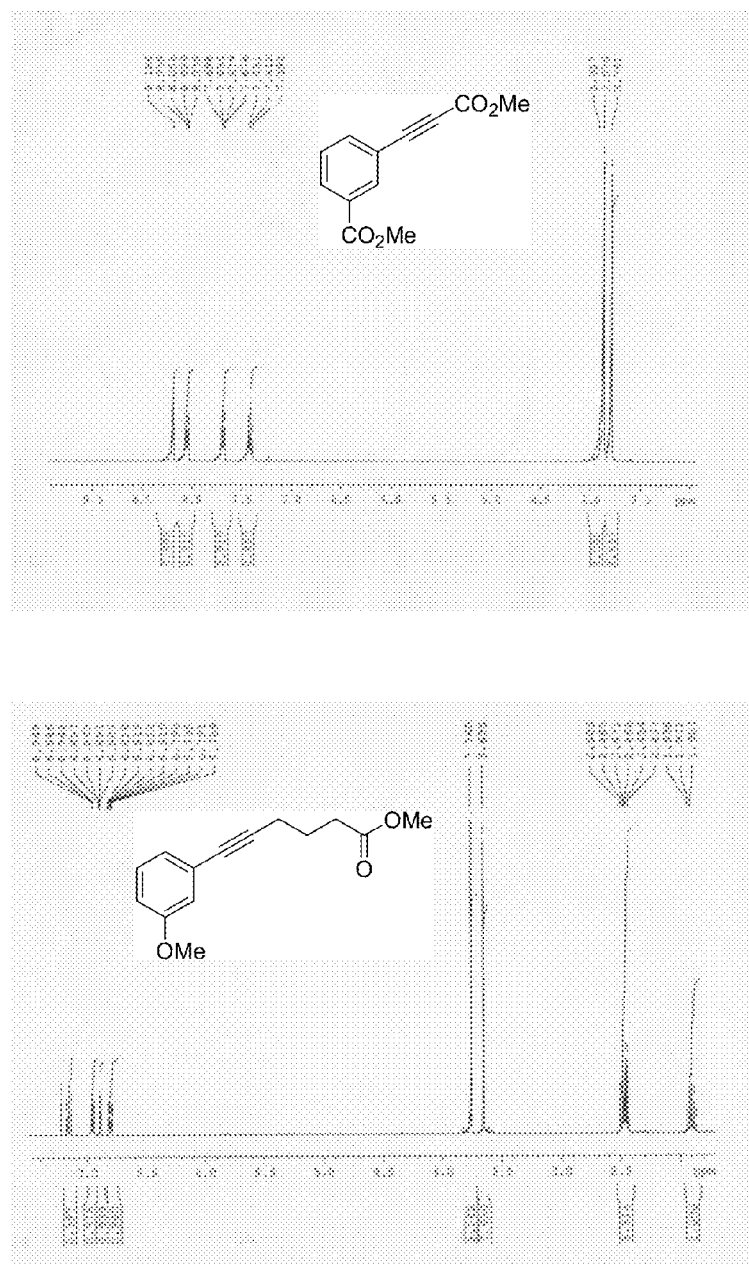
FIG. 8 depicts the $^1$H NMR spectrum (CDCl$_3$) of 3-methoxycarbonylethynyl-benzoic acid methyl ester; and the $^1$H NMR spectra (CDCl$_3$) of 6-(3-methoxy-phenyl)-hex-5-ynoic acid methyl ester.

The general procedure described in Example 27 was used with 3-bromobenzoic acid (101 mg, 0.50 mmol), propiolic acid (added at 0° C.) (0.050 mL, 0.65 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (813 mg, 2.50 mmol), water (1.0 mL), acetonitrile (1.0 mL), 12 h, 60° C. The product was isolated as a white solid (77 mg, 70%). Mp=96-97° C. $^1$H NMR (400 MHz, CDCl$_3$) δ: 8.19 (m, 1H), 8.04 (d, 1H, J=8.0 Hz), 7.68 (d, 1H, J=7.6 Hz), 7.41 (t, 1H, J=7.6 Hz), 3.87 (s, 3H), 3.79 (s, 3H). $^{13}$C NMR (125 MHz, CDCl$_3$) δ: 165.9, 154.3, 136.9, 134.2, 131.7, 130.9, 128.9, 120.1, 85.1, 81.0, 53.0, 52.6. IR (neat, cm$^{-1}$): 3022, 2963, 2231, 1738, 1718, 1437, 1290, 1259, 1197, 1173, 1101, 749. $^1$H NMR (CDCl$_3$) is shown in FIG. 8.

Example 30

Synthesis of 4-dec-1-ynyl-benzoic acid (FIG. 6, Entry 3)

The general procedure described in Example 27 was used with 4-chlorobenzoic acid (79 mg, 0.50 mmol), 1-decyne (0.136 mL, 0.75 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.0 mL), 12 h, 100° C. The product was isolated as a white solid (111 mg, 86%). Mp=103° C. $^1$H NMR (400 MHz, CDCl$_3$) δ: 11.0 (br-s, 1H), 8.04 (d, 2H, J=8.4 Hz), 7.49 (d, 2H, J=8.4 Hz), 2.46 (t, 2H, J=6.8 Hz), 1.64 (p, 2H, J=6.8 Hz), 0.89-1.49 (m, 13H). $^{13}$C NMR (125 MHz, CDCl$_3$) δ: 169.3, 132.6, 130.9, 130.8, 130.4, 94.6, 81.2, 33.2, 30.5, 30.4, 30.2, 29.9, 23.9, 20.2, 14.6 IR (neat, cm$^{-1}$): 3402 (br), 2920, 2849, 2214, 1686, 1607, 1428, 1319, 1283, 1178, 1112, 929, 862, 769. Anal. Calcd for C$_{17}$H$_{22}$O$_2$: C, 79.03; H, 8.58. Found: C, 78.84; H, 8.48.

Example 31

Synthesis of 6-(3-methoxy-phenyl)-hex-5-ynoic acid methyl ester (FIG. 6, Entry 4)

The general procedure described in Example 27 was used with 3-chloroanisole (0.061 mL, 0.50 mmol), 5-hexynoic acid (0.072 mL, 0.65 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.0 mL), 10 h, 100° C. The product was isolated as a colorless oil (60 mg, 85%). $^1$H NMR (400 MHz, CDCl$_3$) δ: 7.16 (t, 1H, J=8.0 Hz), 6.96 (dt, 1H, J=1.2 Hz, 7.6 Hz), 6.89 (m, 1H), 6.80 (qd, 1H, J=1.2 Hz, 2.4 Hz, 8.4 Hz), 3.76 (s, 3H), 3.66 (s, 3H), 2.48 (t, 2H, J=7.2 Hz), 2.45 (t, 2H, J=6.8 Hz), 1.90 (q, 2H, J=6.8 Hz). $^{13}$C NMR (125 MHz, CDCl$_3$) δ: 173.8, 159.4, 129.5, 124.9, 124.3, 116.6, 114.5, 88.9, 81.6, 55.4, 51.8, 33.1, 24.1, 19.1. IR (neat, cm$^{-1}$): 2952, 2232, 1737, 1598, 1574, 1481, 1434, 1316, 1287, 1206, 1164, 1045, 854, 786, 688. $^1$H NMR (CDCl$_3$) is shown in FIG. 8.

Example 32

Synthesis of 3-dec-1-ynyl-2,4-difluoro-benzoic acid (FIG. 6, Entry 5)

The general procedure described in Example 27 was used with 3-chloro-2,4-difluoro-benzoic acid (97 mg, 0.50 mmol), 1-decyne (0.136 mL, 0.75 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.0 mL), 12 h, 100° C. The product was isolated as a white solid (102 mg, 70%). Mp=117° C. $^1$H NMR (400 MHz, d$^6$-DMSO) δ: 10.1 (br-s, 1H), 7.88 (q, 1H, J=8.8 Hz), 7.26 (t, 1H, J=8.4 Hz), 2.51 (t, 2H, J=6.8 Hz), 1.57 (p, 2H, J=6.8 Hz), 0.80-1.43 (m, 13H). $^{13}$C NMR (125 MHz, CDCl$_3$) δ: 168.7, 167.9, 165.3, 162.6, 132.3, 132.2, 114.1, 111.7, 111.5, 104.8, 103.1, 66.7, 32.0, 29.4, 29.3, 28.9, 28.5, 22.9, 20.0, 14.3. IR (neat, cm$^{-1}$): 3428 (br), 2922, 2848, 2235, 1689, 1611, 1406, 1268, 1242, 1051, 1036. Anal. Calcd for C$_{17}$H$_{20}$F$_2$O$_2$: C, 69.37; H, 6.85. Found: C, 69.13; H, 6.80.

Example 33

Synthesis of 1-methoxy-3-(phenylethynyl)-benzene (FIG. 6, Entry 6; W. Shen, W. Le *J. Org. Chem.* 1999, 64, 8873.)

The general procedure described in Example 27 was used with 3-chloroanisole (0.063 mL, 0.50 mmol), phenylacetylene (0.072 mL, 0.65 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.5 mL), 12 h, 100° C. The product was isolated as a white solid (99 mg, 95%). Mp=70° C. (lit. 72-74° C.). $^1$H NMR (400 MHz, CDCl$_3$) δ: 7.62 (m, 2H), 7.41 (m, 3H), 7.32 (t, 1H, J=7.6 Hz), 7.23 (dt, 1H, J=1.2 Hz, 7.6 Hz), 7.15 (m, 1H), 6.96 (qd, 1H, J=1.2 Hz, 2.4 Hz, 7.6 Hz). $^{13}$C NMR (125 MHz, CDCl$_3$) δ: 159.5, 131.8, 129.6, 128.5, 128.48, 124.4, 124.3, 123.3, 116.5, 115.1, 89.5, 89.4, 55.4.

Example 34

Synthesis of 3-(3-thienylethynyl)-pyridine (FIG. 6, Entry 7; I. Novak, S.-C. Ng, C.-Y. Mok, H.-H. Huang, J. Fang, K. K. T. Wang *J. Chem. Soc. Perkin Trans* 2 1994, 1771.)

The general procedure described in Example 27 was used with 3-chloropyridine (0.050 mL, 0.50 mmol), 3-ethynylthiophene (0.074 mL, 0.75 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.5 mL), 10 h, 100° C. The product was isolated as a white solid (86 mg, 93%). Mp=62° C. (lit. 65.5-64.0° C.). $^1$H NMR (400 MHz, CDCl$_3$) δ: 8.75 (d, 1H, J=1.6 Hz), 8.54 (dd, 1H, J=2.0 Hz, 5.2 Hz), 7.79 (dt, 1H, J=8.0 Hz, 2.0 Hz), 7.57 (dd, 1H, J=2.8 Hz, 1.2 Hz), 7.32 (dd, 1H, J=5.2 Hz, 2.8 Hz), 7.27 (qd, 1H, J=0.8 Hz, 4.8 Hz, 3.2 Hz), 7.21 (dd, 1H, J=1.2 Hz, 5.2 Hz). $^{13}$C NMR (125 MHz, CDCl$_3$) δ: 152.4, 148.7, 138.5, 129.9, 129.6, 125.9, 123.2, 121.8, 120.6, 87.9, 85.7.

Example 35

Synthesis of methyl-4-(phenylethynyl)benzoate (FIG. 6, Entry 8; U.-C. Yang, T.-Y. Luh *J. Org. Chem.* 2003, 68, 9870.)

The general procedure described in Example 27 was used with 4-chlorobenzoic acid (79 mg, 0.50 mmol), phenylacetylene (0.072 mL, 0.65 mmol), PdCl$_2$(CH$_3$CN)$_2$ (3.2 mg, 0.0125 mmol, 1.25 mol %), sodium 2'-(dicyclohexyl-phosphanyl)-2,6-diisopropyl-biphenyl-4-sulfonate (20.0 mg, 0.0375 mmol, 3.75 mol %), Cs$_2$CO$_3$ (650 mg, 2.00 mmol), water (1.0 mL), acetonitrile (1.5 mL), 12 h, 100° C. The product was isolated as a white solid (101 mg, 86%). Mp=114° C. (lit. 113-115° C.). $^1$H NMR (400 MHz, CDCl$_3$) δ: 8.04 (d, 2H, J=8.4 Hz), 7.61 (d, 2H, J=8.4 Hz), 7.57 (m, 2H), 7.39 (m, 3H). $^{13}$C NMR (125 MHz, CDCl$_3$) δ: 166.6, 131.9, 131.6, 129.64, 129.56, 128.9, 128.6, 128.1, 122.8, 92.5, 88.8, 52.3.

Incorporation By Reference

Each of the U.S. patents, U.S. patent application publications, and PCT published applications designating the U.S. cited herein is hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claimed:
1. A method represented by Scheme 3:

Scheme 3

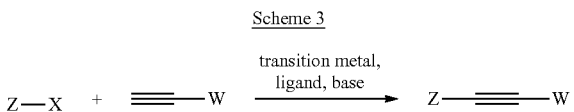

wherein
Z is selected from the group consisting of optionally substituted aryl, heteroaryl and alkenyl;
X is selected from the group consisting of Cl, Br, I, —OS(O)$_2$alkyl, and —OS(O)$_2$aryl;
W is selected from the group consisting of alkyl, —COOH, cycloalkyl, aryl, heteroaryl, aralkyl, heteroaralkyl, —(CH$_2$)$_m$—COOH, and —(CH$_2$)$_m$—R$^{80}$;
Z and W may be covalently linked;
the transition metal is selected from the Group 10 metals;
the base is selected from the group consisting of fluorides, hydrides, hydroxides, carbonates, phosphates, alkoxides, metal amides, and carbanions; and
the ligand is selected from the group consisting of compounds represented by L:

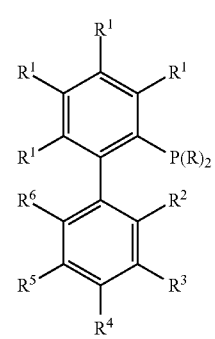

wherein
R is selected independently for each occurrence from the group consisting of alkyl, cycloalkyl, aryl, heteroaryl, aralkyl, heteroaralkyl, and —(CH$_2$)$_m$—R$^{80}$;
R$^1$ is selected independently for each occurrence from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$;

$R^2$ is selected from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$;

$R^3$ is selected from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, $-R^7$, and $-(CH_2)_m-R^{80}$;

$R^4$ is selected from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, $-R^7$, and $-(CH_2)_m-R^{80}$;

$R^5$ is selected from the group consisting of hydrogen, halogen, alkyl, cycloalkyl, heterocycloalkyl, aryl, heteroaryl, aralkyl, heteroaralkyl, $-OR^B$, $-N(R^8)_2$, $-Si(R^8)_3$, $-R^7$, and $-(CH_2)_m-R^{80}$;

$R^6$ is selected from the group consisting of hydrogen, halogen, alkyl, cycloalkyl, heterocycloalkyl, aryl, heteroaryl, aralkyl, heteroaralkyl, $-OR^8$, $-N(R^8)_2$, $-Si(R^8)_3$, and $-(CH_2)_m-R^{80}$;

$R^7$ is selected independently for each occurrence from the group consisting of $-C(O)OM$, $-C(O)SM$, $-C(S)SM$, $-C(NR^8)OM$, $-C(NR^8)SM$, $-S(O)OM$, $-S(O)SM$, $-S(O)_2OM$, $-S(O)_2SM$, $-P(O)(OM)_2$, $-P(O)(OR^8)OM$, $-P(O)(OR^8)NR^8M$, $-P(O)(OR^8)SM$, $-N(R^8)_3M$, $-P(R^8)_3M$, $-P(OR^8)_3M$, and $-N(R^8)C(NR^8R^8)NR^8R^8M$;

$R^8$ is selected independently for each occurrence from the group consisting of hydrogen, alkyl, cycloalkyl, heterocycloalkyl, aryl, heteroaryl, aralkyl, and heteroaralkyl;

M is an alkali metal or an alkali earth metal;

$R^{80}$ represents an unsubstituted or substituted aryl, a cycloalkyl, a cycloalkenyl, a heterocycle, or a polycycle;

m is independently for each occurrence an integer in the range 0 to 8 inclusive;

provided that at least one of $R^3$, $R^4$, or $R^5$ is $R^7$; and the ligand is achiral, or when chiral, is a single stereoisomer or a mixture of stereoisomers.

2. The method of claim 1, wherein the transition metal is palladium.

3. The method of claim 2, further comprising irradiating with microwave radiation.

4. The method of claim 2, wherein R is cyclohexyl; $R^1$ is hydrogen; $R^2$ and $R^6$ are selected independently from the group consisting of hydrogen, alkyl and alkoxy; $R^3$ is $R^7$; and $R^4$ and $R^5$ are hydrogen.

5. The method of claim 2, wherein R is cyclohexyl; $R^1$ is hydrogen; $R^2$ and $R^6$ are selected independently from the group consisting of hydrogen, alkyl and alkoxy; $R^4$ is $R^7$; and $R^3$ and $R^5$ are hydrogen.

6. The method of claim 2, wherein R is cyclohexyl; $R^1$ is hydrogen; $R^2$ and $R^6$ are methoxy; $R^3$ is $-S(O)_2ONa$; and $R^4$ and $R^5$ are hydrogen.

7. The method of claim 2, wherein R is cyclohexyl; $R^1$ is hydrogen; $R^2$ and $R^6$ are isopropyl; $R^4$ is $-S(O)_2ONa$; and $R^3$ and $R^5$ are hydrogen.

* * * * *